US005955293A

United States Patent [19]
Keusch et al.

[11] Patent Number: 5,955,293
[45] Date of Patent: Sep. 21, 1999

[54] ASSAYS FOR SHIGA TOXIN AND SHIGA-LIKE TOXINS

[75] Inventors: Gerald T. Keusch, Lexington; Arthur Donohue-Rolfe, Sudbury; David W. K. Acheson, Norwood, all of Mass.

[73] Assignee: New England Medical Center Hospitals, Inc., Boston, Mass.

[21] Appl. No.: 08/243,539

[22] Filed: May 16, 1994

Related U.S. Application Data

[63] Continuation of application No. 07/950,846, Sep. 24, 1992, abandoned, which is a continuation-in-part of application No. 07/517,868, May 2, 1990, abandoned, which is a continuation-in-part of application No. 07/422,485, Oct. 17, 1989, abandoned.

[51] Int. Cl.⁶ .......................... G01N 33/53; C07K 16/00
[52] U.S. Cl. ...................... 435/7.92; 435/7.32; 435/7.94; 435/7.95; 435/975; 435/70.21; 435/340; 530/388.4
[58] Field of Search .......................... 435/38, 7.37, 7.92, 435/7.94, 7.95, 70.1, 7.2, 7.21, 326, 340, 975, 7.32; 436/518; 530/388.1, 388.4

[56] References Cited

U.S. PATENT DOCUMENTS 4,981,685  1/1991  Healey ................................. 424/203.1

OTHER PUBLICATIONS

Keusch et al., "Shigella Toxin(s): Description and Role in Diarrhea and Dysentery," *Pharmac. Ther.* (1982) 15:403–438.

O'Brien et al., "*Escherichia coli* O157:H7 Strains Associated with Haemorrhagic Colitis in the United States Produce a *Shigella Dysenteriae* 1 (Shiga) like Cytotoxin," *Lancet* i:702–703.

Keusch et al., "Shiga Toxin: Production and Purification," *Methods in Enzymology* (1988) 165:152–163; 399–401.

Keusch et al., "The Pathogenesis of Shigella Diarrhea: Enterotoxin Production by *Shigella Dynsenteriae* 1," *J. Clin. Invest.* (1972) 51:1212–1218.

Keusch et al., "Quantitative Microassay in Cell Culture for Entertoxin of *Shigella dysenteriae* 1," *J. Infect. Dis.* (1972) 125:539–541.

Cameron et al., "Blood Group P Substance in Hydatid Cyst Fluids," *Nature* (1957) 179:147–148.

Köhler et al., "Continuous Cultures of Fused Cells Secreting Antibody of Predefined Specificity," *Nature* (1975) 256:495–497.

Marcus et al., "The P Blood Group System: Recent Progress in Immunochemistry and Genetics," *Seminars in Hematology* (1981) 18:63–71.

Teng et al., "Construction and Testing of Mouse–Human Heteromyelomas for Human Monoclonal Antibody Production," *Proc. Natl. Acad. Sci. USA* (1983) 80:7308–7312.

Kozbor et al., "The Production of Monoclonal Antibodies From Human Lymphocytes," *Immunology Today* (1983) 4:72–79.

Cory et al., "The Nature of the Human Blood Group P¹ Determinant," *Biochem. Biophys. Res. Comm.* (1974) 61:1289–1296.

Olsson et al., "Human–Human Monoclonal Antibody–Producing Hybridomas: Technical Aspects," *Methods in Enzymology* (1983) 92:3–16.

Cole et al., "The EBV–Hybridoma Technique and its Application to Human Lung Cancer," *Monoclonal Antibodies and Cancer Therapy*, Alan R. Liss, Inc., (1985) pp. 77–96.

Keusch et al., "Shigella Toxin and the Pathogenesis of Shigellosis," *Ciba Foundation Symp.* (1985) 112:193–214.

Reisbig et al., "The Cytotoxic Activity of Shigella Toxin," *J. Biol. Chem.* (1981) 256:8739–8744.

Scotland et al., "Two Distinct Toxins Active on Vero Cells from *Escherichia coli* O157," *Lancet* (1985) ii:885–886.

O'Brien et al., "Shiga and Shiga–Like Toxins," *Microbiol. Rev.* (1987) 51:206–220.

O'Brien et al., "Shiga–Like Toxin–Converting Phages from *Escherichia coli* Strains That Cause Hemorrhagic Colitis or Infantile Diarrhea," *Science* (1984) 226:694–696.

Donohue–Rolfe et al., "Isolation and Characterization of Functional Shiage Toxin Subunits and Renatured Holotoxin," *Molecular Microbiology* (1989) 3:1231–1236.

Riley et al., "Hemorrhagic Colitis Associated with a Rare *Escherichia coli* Serotype," *New Engl. J. Med.* (1983) 308:681–685.

Endo et al., "Site of Action of a Vero Toxin (VT2) from *Escherichia coli* O157:H7 and of Shiga Toxin on Eukaryotic Ribosomes," *Eur. J. Biochem.* (1988) 171:45–50.

Head et al., "Serological Differences between Verocytotoxin 2 and Shiga–like Toxin II," *Lancet* (1988) ii:751.

Igarashi et al., "Inhibition of Elongation Factor 1–Dependent Aminoacyl–tRNA Binding to Ribosomes by Shiga–like Toxin I (VT1) from *Escherichia coli* O157:H7 and by Shiga–Toxin," *FEMS Microbiol Letters* (1987) 44:91–94.

(List continued on next page.)

*Primary Examiner*—Patricia A. Duffy
*Attorney, Agent, or Firm*—Fish & Richardson, P.C.

[57] ABSTRACT

The present invention relates to a substantially pure antigenic peptide or protein related to Shiga toxin, Shiga-like toxin I, Shiga-like toxin II or a variant of Shiga-like toxin II, and to a vaccine formulation containing such a peptide or protein useful in treating a disease associated with the toxin. Also disclosed is a method for treating a disorder associated with the expression of Shiga toxin or a Shiga-like toxin using an effective amounts of the P1 glycoprotein. Antibodies may be generated to Shiga-like toxin II of the present invention that cross-react with Shiga toxin and Shiga-like toxin I. Also disclosed are methods for removing Shiga toxin or a Shiga-like toxin from a sample such as a body fluid using the antibody or the P1 glycoprotein. Also provided are methods and kits for detecting disorders associated with the expression of Shiga toxins and Shiga-like toxins I and II involving the detection of the toxins.

20 Claims, 10 Drawing Sheets

OTHER PUBLICATIONS

Jackson et al., "Nucleotide Sequence Analysis and Comparison of the Structural Genes for Shiga–like Toxin I and Shiga–like Toxin II encoded by Bacteriophages from *Escherichia coli* 933," *FEMS Microbiol Letters* (1987) 44:109–114.

Pouch Downs et al., "Affinity Purification and Characterization of Shiga–Like Toxin Ii and Production of Toxin–Specific Monoclonal Antibodies," *Infect. Immunity* (1988) 56:1926–1933.

Konowalchuk et al., "Vero Response to a Cytotoxin of *Escherichia coli*," *Infect. Immunity* (1977) 18:775–779.

Strockbine et al., "Cloning and Sequencing of the Genes for Shiga Toxin from *Shigella dysenteriae* Type I," *J. Bacteriology* (1988) 170:1116–1122.

Jacewicz et al., "Isolation of a Shigella Toxin–Binding Glycolipid from Rabbit Jejunum and HeLa Cells and Its Identification as Globotriaosylceramide," *J. Exp. Med.* (1986) 163:1391–1404.

Donohue–Rolfe et al., "Pathogenesis of Shigella Diarrhea:Simplified High Yield Purification of Shigella Toxin and Characterization of Subunit Composition and Function by the Use of Subunit–specific Monoclonal and Polyclonal Antibodies," *J. Exp. Med.* (1984) 160:1767–1781.

Donohue–Rolfe, A; Kelly, M.A.; Bennish, M. and Keusch, G.T. Enzyme–linked Immunosorbent Assay for Shigella Toxin Journal of Clinical Microbiology 24(1) 65–68, 1986.

Brown, J.E.; Echeverria, P.; Lindberg, A.A.; Digalactosyl–containing glycolipids as cell–surface receptors for Shiga Toxin of *Shigella dysenteriae* 1 and related cytotoxins of *Escherichia coli* Reviews of Infectious Disease 13(suppl.4):S298–303, 1991.

Gannon, V.P.; Teerling, Masri, S.A; and Gyles, C.L. Molecular cloning and nucleotide sequencing of another variant of the *Escherichia coli* shiga–like Toxin II family. Journal of General Microbiology 136:1125–1135, 1990.

Weinstein, D.L.; Jackson, M.P.; Samuel, J.E.; Holmes, R.K.; and O'Brien, A.D. Cloning and sequencing of Shiga–like Toxin Type II variant from *Escherichia coli* strain responsible for Edema disease of swine. Journal of Bacteriology 170(9):4223–4230. 1988.

Perera, L.P; Marques, L.R.M.; and O'Brien, A.D. Isolation and characterization of monoclonal antibodies to shiga–like toxin II of enterohemorrhagic *Escherichi coli* and use of monoclonal antibodies in a colony enzyme–linked immunosorbent assay. Journal of Clinicl Microbiology 26(10):2127–2131, 1988.

Campbell, A.M. Monclonal Antibody Technology: The Production and characterization of Rodent and Human Hybridomas. New York, Elsevier, 1987. Chapter 1, pp. 1–32.

Samuel, J.E., Perera, L.P.; Ward, S.; O'Brien, A.D.; Ginsburg, V.; and Krivan, H.C. Comparison of the glycolipid receptor specificities of Shiga–like Toxin Type II and Shiga–like Toxin Type II variants. Infection and Immunity 58(3):611–618, 1990.

Ashkenazi, S. and Cleary, T.G. Rapid method to detect Shiga Toxin and Shiga–Like Toxin I based on binding to globotriasyl ceramide ($Gb_3$), their natural receptor. Journalof Clinical Microbiology 27(6):1145–1150, 1989.

Oku, Y.; Yutsudo, T, Hirayama, T.; O'Brien, A.D.; and Takeda, Y. Purification and some properties of a verotoxin from a human strain of *Escherchia coli* that is immuno–logically related to shiga–like Toxin II (VT2). Microbiol. Pathogenesis 6:113–122, 1989.

Achesou, D.W.K; Keusch, GT; Lightowlers, M.; and Donohue–Rolfe, A. Enzyme–linked immunosorbent assay for Shiga Toxin & Shiga–like Toxin II using P1Glycoprotein from hydatid cysts. The Journal of Infectious Disesaes 161:134–137, 1990.

DeGrandis, S.; Law, H.; Brunton, J.; Gyles, C.; and Lingwood, C.A.; Globotetraosylceramide is recognized by the pig edema disease toxin. Journal of Biological Chemistry 264(21) 12520–12525.

Donohue–Rolfe et al., Infection and Immunity 57:12 3888–3893 1989.

Campbell, A.M., "Monoclonal Antibody and Immunosensor Technology" in vol. 23 Laboratory Techniques in Biochemistry and Molecular Biology, 1991 by Elsevier, NY, pp. 1–7.

FIG. 1

Toxin Bound (% of Control) vs Hydatid Cyst Protein (ng/ml)

FIG. 2

% Leucine Incorporation and % Toxin Bound vs Hydatid Cyst Protein (ng/ml)

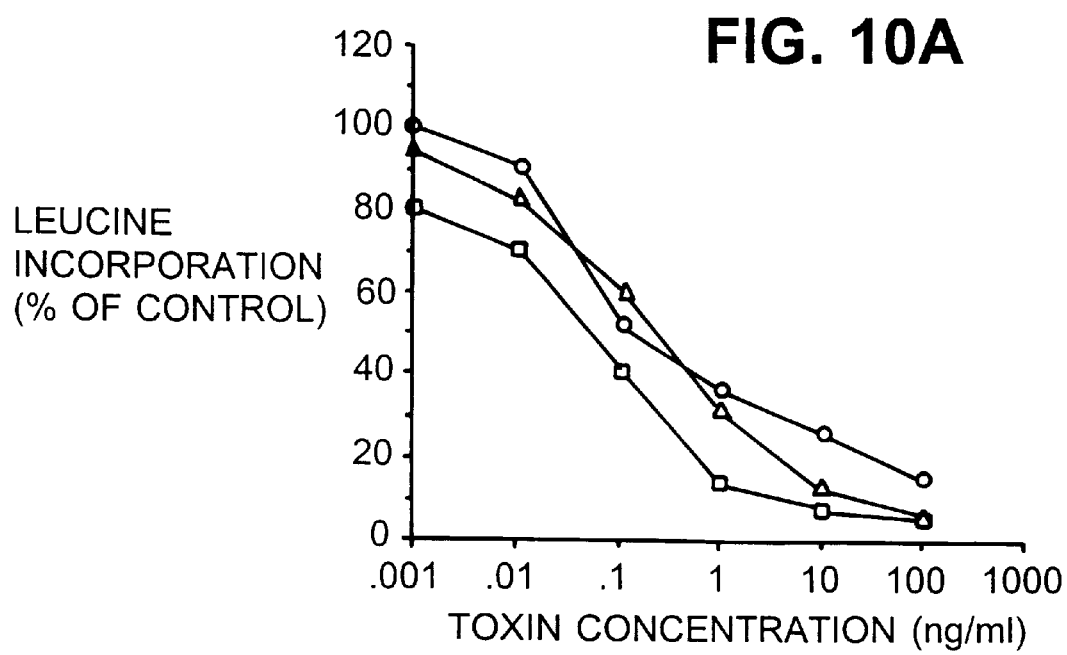
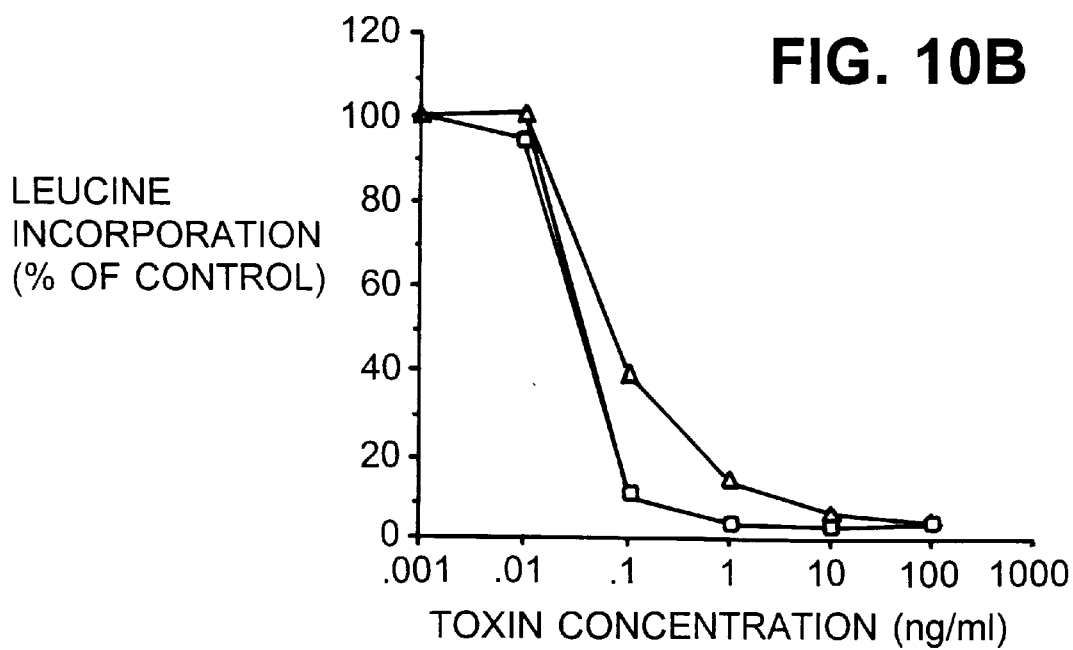

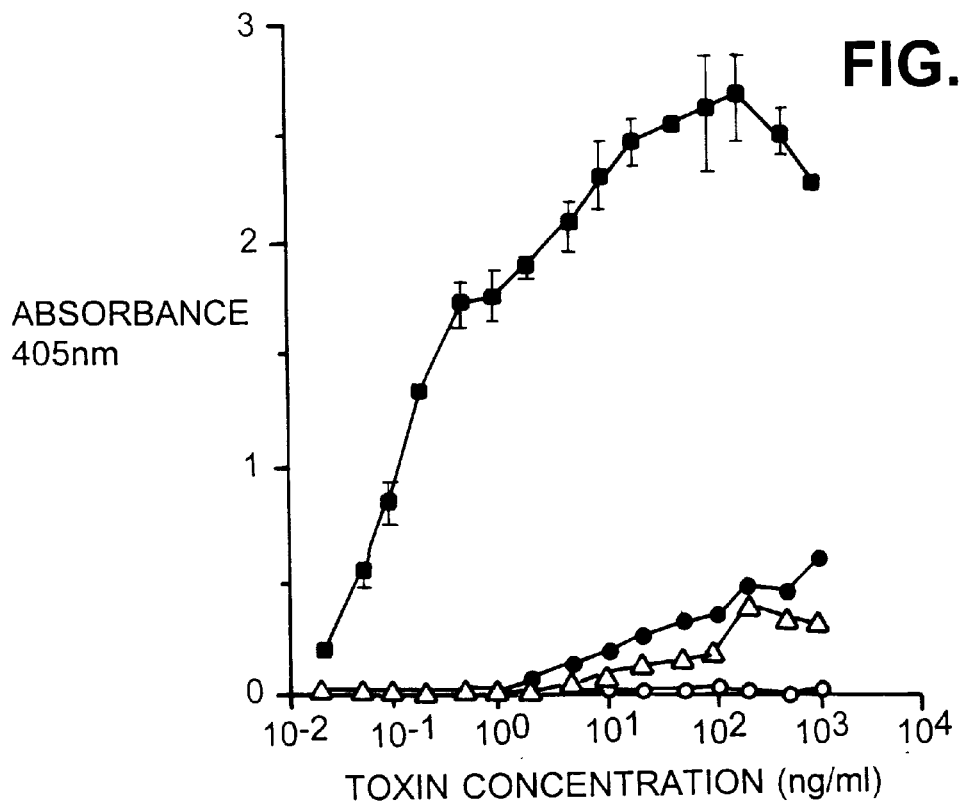
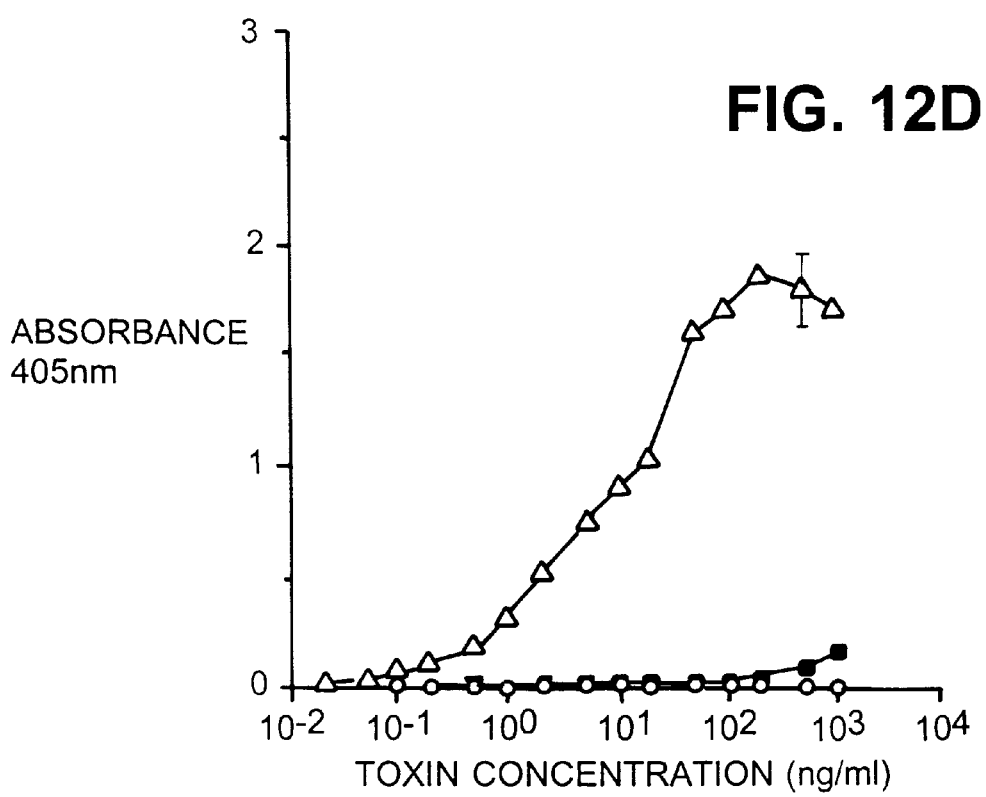

ASSAYS FOR SHIGA TOXIN AND SHIGA-LIKE TOXINS

CROSS REFERENCE TO RELATED APPLICATIONS

This is a continuation of application Ser. No. 07/950,846, filed Sep. 24, 1992, now abandoned, which is a continuation-in-part of application Ser. No. 07/517,868 filed May 2, 1990, now abandoned, which is a continuation-in part of application Ser. No. 07/422,485 filed Oct. 17, 1989, now abandoned.

This invention was funded in part by research grants from the National Institutes of Health (AI 16242, AI 20235 and DK 34928), which provides to the United States Government certain rights in this invention.

1. FIELD OF INVENTION

The present invention is directed to a substantially pure antigenic peptide or protein related to Shiga toxin (ST), Shiga-like toxin I (SLT-I), Shiga-like toxin II (SLT-II) or SLT-II variants. ST, SLT-I, SLT-II and SLT-II variants are useful in subunit vaccine formulations. Also provided are antibodies to SLT-II epitopes which cross-react with ST and SLT-I.

The invention is also directed to a affinity binding method for removing ST, SLT-I, SLT-II and SLT-II variants from a sample, such as a biological fluid. Such methods are also used to obtain substantially pure toxin molecules for use in vaccine formulations. Alternatively the method may be used to treat or prevent disorders associated with these toxins by removing them from bodily fluids.

The present invention is further directed to methods and kits for detecting ST, SLT-I, SLT-II and SLT-II variants. Such methods and kits may be useful for the detection of disorders associated with the expression of these toxins.

The invention also relates to the use of effective amounts of P1 glycoprotein, appears to act as a receptor for ST, SLT-I, SLT-II and SLT-II variants, for the treatment of disorders associated with the expression of these toxins.

2. BACKGROUND OF THE INVENTION

2.1. SHIGA TOXIN

Shiga toxin (ST) is a multimeric protein toxin produced by the bacterium *Shigella dysenteriae* type I. It was first described in 1903 in the prototypic species, *Shigella dysenteriae* type I (Conradi, *Dtsch. Med. Wochenschr.* 20:26–28 (1903)). Parenteral injection of ST into susceptible animals results in a delayed limb paralysis followed by death (Keusch et al., 1982, *Pharmacol. Ther.* 15a:402–435). ST is thought to play a significant role in the pathogenesis of Shigellosis (Keusch et al., 1982, supra; Keusch et al., 1985, *Ciba Foundation Symp.* 112:193–214). ST has multiple biological activities including enterotoxicity, neurotoxicity, and cytotoxicity (Keusch et al., 1982, supra) and is a potent inhibitor of protein synthesis through the inactivation of the 60S ribosomal subunit (Reisbig, et al., 1981, *J. Biol. Chem.* 2566:8739–8749).

A molecule of ST consists of one 32 kDa polypeptide chain (termed the A chain) and five 7.6 kDa polypeptide chains (termed the B chain) (Donohue-Rolfe et al., *J. Exp. Med.* 160:1767–1781 (1984); Donohue-Rolfe et al., *Molec. Microbiol.* 3:1231–1236 (1989)) The A chain is responsible for the ST's ability to inhibit protein synthesis (Igarashi et al., 1987, FEMS Microbiol. Lett. 44:91–94). Jacewicz et al. (1986, *J. Exp. Med.* 163:1391–1404) demonstrated that ST binds specifically via its B chain subunit to a glycolipid present in both rabbit jejunal mucosa and in human HeLa cells. This receptor has been identified as globotriaosylceramide (Gb3), Gal$\alpha$1→4Gal$\beta$1→4Glc$\beta$1-Ceramide. ST also binds to the P1 blood group antigen present in human erythrocyte glycolipid extracts. Common to both Gb3 and P1 antigen is a terminal Gal$\alpha$1-4Gal disaccharide.

Over the last decade, ST has been purified to homogeneity (reviewed in Keusch et al., *Methods In Enzymology* 165:152–162, 399–401 (1988)). Examples of purification methods include gel-exclusion chromatography, antibody affinity chromatography, chromatofocusing, and/or Blue Sepharose chromatography. ST has most commonly been detected by: its lethality in vivo, using $LD_{50}$ measurements; its enterotoxic activity using measurement of fluid secretion in rabbit intestine (Keusch et al., 1972, J. Clin. Invest. 51:1212–1218); or cytotoxic activity measuring tissue culture $LD_{50}$ (Keusch et al., 1972, J. Infect. Dis. 125:539–541). Recently, the present inventors developed a method for detecting ST using an ELISA assay, employing a mouse monoclonal antibody (mAb) specific for the ST B subunit and a rabbit polyclonal antibody specific for the holotoxin (Donohue-Rolfe et al., 1986, J. Clin. Microbiol. 24:65–68). Though the ELISA method is sensitive, to 12 pg of toxin/well, it is somewhat tedious, requiring two types of antibodies.

2.2. SHIGA-LIKE TOXINS I AND II

Cytotoxins with biological properties similar to ST have been identified in a variety of bacterial species, including *E. coli*, Vibrio, Salmonella, and Campylobacter species (O'Brien et al., 1987, Microbiol. Rev. 151:206–220). In 1977, an *E. coli* toxin, designated "Verotoxin", was reported to be cytotoxic to Vero cells and distinct from the well-known heat labile and heat stable *E. coli* toxins (Konowalchuk, 1977, Infect. Immun. 18:775–779). This toxin and the *E. coli* strains producing it are associated with the diseases of hemolytic uremic syndrome and hemorrhagic colitis (Riley et al., 1983, N. Engl. J. Med. 308:681–685).

Because the cytotoxin produced by *E. coli* 0157:H7, a strain associated with hemorrhagic colitis, was neutralized by an antiserum raised against Shiga toxin, it was designated "Shiga-like toxin" (O'Brien et al. 1983, Lancet i:702–703). Further studies of *E. coli* 0157:H7 strain 933 revealed two toxin converting phages termed 933J and 933W (O'Brien et al., 1984, Science, 226:694–696). *E. coli* 0157:H7 produced two cytotoxins, only one of which could be neutralized by antisera to ST (Scotland et al., 1985, Letter, Lancet ii:885–886). These toxins have been designated Shiga-like toxin I and II (SLT-I and SLT-II) respectively (Strockbine et al., 1988, J. Bacteriol. 170:1116–1122).

SLT-I encoded by phage 933J predominates in *E. coli* 0157:H7 cell lysates, whereas SLT-II encoded by phage 933W predominates in culture supernatants (Strockbine et al., supra). SLT-I and SLT-II share the biological activities of neurotoxicity in mice, enterotoxicity in ligated rabbit ileal segments and cytotoxicity to both Vero and HeLa cells (Strockbine et al., supra). ST, SLT-I and SLT-II all inhibit protein synthesis by inactivating the 60S ribosomal subunit. All three toxins cleave the N-glycosidic bond at A-4324 in 28S ribosomal RNA (Endo et al., 1988, Eur. J. Biochem. 171:45–50), thus indicating conservation of the active enzymatic site in the A subunits of these toxins.

Nucleotide sequencing of the toxin genes has shown that the mature ST and SLT-I proteins differ by only one amino acid substitution in the A subunit (Strockbine, 1988, supra). SLT-I and SLT-II, however, are only 58% homologous at the nucleotide level and 56% homologous at the amino acid level (55% A subunit homology and 57% B subunit homology) (Jackson et al., 1987, FEMS Microbiol. Lett. 44:109–114). SLT-II consists of A and B subunits, although its precise subunit stoichiometry has not been clearly defined.

Despite the common functional attributes of ST, SLT-I and SLT-II, the lack of neutralizing immunologic cross-reactivity has resulted in a separation into two groups (ST and SLT-I vs. SLT-II) (Perera et al., 1988, J. Clin. Microbiol. 26:2127–2131 and Pouch-Downes et al., 1988, Infect. Immun. 56:1926–1933). Since ST, SLT-I and SLT-II bind to the same receptor, and since the toxins' binding domain is exposed on the surface, an antibody directed against the binding domain of one of these toxins would be expected to cross-react with the other related molecules. Similarly, the identical and highly specific mechanism of action of the A subunits of the three toxins predicts a conserved sequence of the active enzymatic site which could induce cross-reactive antibodies. These features make the initially reported apparent lack of immunological cross-reactivity between ST/SLT-I and SLT-II puzzling. Recently, a mAb against SLT-II was found to cross-neutralize SLT-I from $E.$ $coli$ strain H30 (Donohue-Rolfe et al., $Infec.$ $Immun.$ 57:3888–3893 (1989)).

As more members of the SLT family have been described and new nomenclature proposed, the field has become increasingly complex and confused. It is now clear that certain $E.$ $coli$ strains contain a second toxin operon which encodes a toxin that is closely related to SLT-II, which has been designated SLT-IIc (Schmitt, C. K. et al., $Infect.$ $Immun.$ 59:1065–1073 (1991)). Oku, Y. et al., $Microb.$ $Path.$ 6:113–122 (1989) had described an SLT from a human clinical isolate of $E.$ $coli$ 91:H21, strain B2F1, which, while immunologically related to SLT-II, was significantly more cytotoxic to Vero cells than to HeLa cells. This SLT was therefore designated an SLT-II variant of human origin (SLT-IIvh). Subsequently Ito, H. et al., $Microb.$ $Pathog.$ 8:47–60 (1990), found that $E.$ $coli$ 091:H21, strain B2F1, contained two SLT-II toxin operons, one of which was very similar to SLT-IIc described by Schmitt et al., (supra). Gannon, V.P.J. et al., $J.$ $Gen.$ $Microb.$ 136:1125–1135 (1990), also isolated an SLT-IIvh, designated SLT-IIva which was closely related to an SLT-II variant of porcine origin.

At least one SLT, associated with porcine disease (edema disease of swine), is biologically very similar to the other SLT-II toxins, was not neutralized by antisera to ST and SLT-I and was reported to be more cytotoxic to Vero cells than to HeLa cells. This toxin has been designated SLT-II variant-porcine (SLT-IIvp) (Marques, L.R.M. et al., $FEMS$ $Micro.$ $Lett.$ 44:33–38 (1987); Weinstein, D. L. et al., $J.$ $Bacteriol$ 170:4223–4230 (1988)).

Differences in cytotoxicity of these toxins for different target cell types may be related to their differential binding to different glycolipid receptors. ST, SLT-I and SLT-II bind preferentially to Gb3, whereas SLT-IIvp, the porcine edema toxin, binds preferentially to globotetraosylceramide (Gb4), although it also binds to Gb3 (DeGrandis, S. et al., $J.$ $Biol.$ $Chem.$ 264:12520–12525 (1989); Samuel, J. E. et al., $Infect.$ $Immun.$ 58:611–618 (1990)). The common binding moiety for SLT's, the a1→4 linked galactose disaccharide, is terminal in Gb3 (Galα1→Galβ1→4Glc-Ceramide) whereas it is internal in Gb4 (GalNAcβ1→3Galα1→4Galβ1→4Glc-Ceramide). Samuel et al. (supra) found that SLT-IIvh isolated from strain B2F1 bound strongly to galabiosylceramide, Ga2 (Galα1→4Galβ1—1Ceramide), and to Gb3, but not to larger glycolipids.

2.3. P1 GLYCOPROTEIN

The P1 glycolipid antigen in human erythrocytes forms part of the P blood group system described many years ago by Landsteiner and Levine (Landsteiner et al., 1927, Proc. Soc. Exp. Biol. Med. 24:941–942). Th P system is now known to consist of three antigens (P1, P and Pk) and at least five phenotypes (P1, P2, P, P1K and P2k) (Marcus, 1981, Sem. Hematol. 18:6371). In 1957 it was reported that material from $Echinococcus$ $granulosus$ hydatid cysts, later identified as a glycoprotein (Morgan, 1964, $Proc.$ $9th$ $Cong.$ $Int.$ $Soc.$ $Blood$ $Transf.$, Mexico, 1962, pp. 225–229; Cameron et al., 1957, $Nature$ 179:147–148), exhibited P1 blood group reactivity and was a competitive inhibitor of the hemagglutination of P1 positive erythrocytes by typing antisera. Thus, the cysts containing live scolices of the tapeworm $Echinococcus$ $granulosus$ provide a relatively convenient source of soluble P1-active substance. The P1gp antigenic determinant was subsequently shown to be a trisaccharide (Galα1→4Galβ1→4GlcNac) identical to the non-reducing end of the P1 glycolipid on human erythrocytes (Cory et al., 1974, $Biochem.$ $Biophys.$ $Res.$ $Comm.$ 61:1289–1296).

3. SUMMARY OF THE INVENTION

The present invention is directed to a substantially pure antigenic peptide or protein related to a Shiga toxin which peptide or protein is obtained from a culture of bacteria, preferably Shigella or any organism, which produce the toxin or related peptide or protein, for example, by expressing a cloned Shiga toxin gene. THe substantially pure peptide or protein is obtained by a method comprising:

(a) concentrating the bacteria, or the organisms expressing a Shiga toxin gene, to produce a bacterial cell pellet and a supernatant;

(b) applying the supernatant to an affinity column having P1 glycoprotein bound to a solid phase support; and (c) eluting from the support any material which bound to the P1 glycoprotein, thereby producing the substantially pure peptide or protein.

In another embodiment, the present invention provides a substantially pure antigenic peptide or protein related to a Shiga toxin, which peptide or protein is obtained from a culture of bacteria producing the toxin, or related protein or peptide, the substantially pure peptide or protein being produced by a method comprising:

(a) concentrating the bacteria to produce a bacterial cell pellet and a supernatant;

(b) precipitating proteins in the supernatant with ammonium sulfate to produce a precipitate;

(c) suspending the precipitate in a buffer, preferably 5 mM–20 mM Tris(hydroxy)methyl aminomethane hydrochloride, pH 7.0–8.0, to form a suspension;

(d) dialyzing the suspension against the buffer to form a solution;

(e) applying the solution to an affinity column in which P1 glycoprotein is bound to a solid phase support; and (f) eluting from the support any material which bound to the P1 glycoprotein, thereby producing the substantially pure peptide or protein.

Also provided is a substantially pure antigenic peptide or protein related to a Shiga toxin, which peptide or protein is obtained from a culture of bacteria producing the toxin or the related peptide or protein, the substantially pure peptide or protein being produced by a method comprising:

(a) concentrating the bacteria to produce a bacterial cell pellet and a supernatant;

(b) physically disrupting the bacteria in the pellet, preferably by sonication, grinding, or homogenization, to produce a lysate;

(c) applying the lysate to an affinity column in which P1 glycoprotein is bound to a solid phase support; and (d) eluting from the support any material which bound to the P1 glycoprotein, thereby producing the substantially pure peptide or protein.

In another embodiment is provided a substantially pure antigenic peptide or protein related to a Shiga toxin, the peptide or protein obtained from a culture of bacteria producing the toxin or related peptide or protein, the substantially pure peptide or protein being produced by a method comprising:
(a) concentrating the bacteria to produce a bacterial cell pellet and a supernatant;
(b) physically disrupting the bacteria in the pellet to produce a lysate;
(c) precipitating the proteins in the lysate with ammonium sulfate to produce a precipitate;
(d) suspending the precipitate in a buffer, preferably 5 mM–20 mM Tris(hydroxy)methyl aminomethane hydrochloride, pH 7.0–8.0, to form a suspension;
(e) dialyzing the suspension against the buffer to form a solution;
(f) applying the solution to an affinity column in which P1 glycoprotein is bound to a solid phase support; and
(g) eluting from the support any material which bound to the P1 glycoprotein, thereby producing the substantially pure peptide or protein.

The bacteria above are preferably Shigella, more preferably of the species Shigella dysenteriae type 1.

The present invention is also directed to a substantially pure antigenic peptide or protein related to Shiga-like toxin I, which peptide or protein is obtained from a culture of bacteria by a method comprising:
(a) concentrating the bacteria to produce a bacterial cell pellet and a supernatant;
(b) applying the supernatant to an affinity column in which P1 glycoprotein is bound to a solid phase support; and
(c) eluting from the support any material which bound to the P1 glycoprotein, thereby producing the substantially pure peptide or protein.

In another embodiment is provided a substantially pure antigenic peptide or protein related to Shiga-like toxin I, the peptide or protein obtained from a culture of bacteria by a method comprising:
(a) concentrating the bacteria to produce a bacterial cell pellet and a supernatant;
(b) precipitating proteins in the supernatant with ammonium sulfate to produce a precipitate;
(c) suspending the precipitate in a buffer, preferably 5 mM–20 mM Tris(hydroxy)methyl aminomethane hydrochloride, pH 7.0–8.0, to form a suspension;
(d) dialyzing the suspension against the buffer to form a solution;
(e) applying the solution to an affinity column in which P1 glycoprotein is bound to a solid phase; and
(f) eluting from the solid phase any material which bound to the P1 glycoprotein, thereby producing the substantially pure peptide or protein.

Also included is a substantially pure antigenic peptide or protein related to Shiga-like toxin I, the peptide or protein obtained from a culture of bacteria by a method comprising:
(a) concentrating the bacteria to produce a bacterial cell pellet and a supernatant;
(b) physically disrupting the bacteria in the pellet, preferably by sonication, grinding, or homogenization, to produce a lysate;
(c) applying the lysate to an affinity column in which P1 glycoprotein is bound to a solid phase support; and
(d) eluting from the support any material which bound to the P1 glycoprotein, thereby producing the substantially pure peptide or protein.

In another embodiment, the invention is directed to a substantially pure antigenic peptide or protein related to Shiga-like toxin I, the peptide or protein obtained from a culture of bacteria by a method comprising:
(a) concentrating the bacteria to produce a bacterial cell pellet and a supernatant;
(b) physically disrupting the bacteria in the pellet, preferably by sonication, grinding, or homogenization to produce a lysate;
(c) precipitating the proteins in the lysate with ammonium sulfate to produce a precipitate;
(d) suspending the precipitate in a buffer, preferably 5 mM–20 mM Tris(hydroxy)methyl aminomethane hydrochloride, pH 7.0–8.;
(e) dialyzing the suspension against the buffer to form a solution;
(f) applying the solution to an affinity column in which P1 glycoprotein is bound to a solid phase support; and
(g) eluting from the support any material which bound to the P1 glycoprotein, thereby producing the substantially pure peptide or protein.

Also provided is a substantially pure antigenic peptide or protein related to Shiga-like toxin IIvp obtained from a culture of bacteria capable of producing Shiga-like toxin IIvp or a protein or peptide related thereto, the substantially pure antigenic protein or peptide obtained by a method comprising:
(a) obtaining a culture supernatant from a culture of the bacteria;
(b) applying the supernatant to an affinity column in which P1 glycoprotein is bound to a solid phase support; and
(c) eluting from the support any material which bound to the P1 glycoprotein, thereby producing the substantially pure peptide or protein.

The present invention also includes a substantially pure antigenic peptide or protein related to Shiga-like toxin IIvp obtained from a culture of bacteria capable of producing Shiga-like toxin IIvp or a protein or peptide related thereto, the substantially pure antigenic protein or peptide obtained by a method comprising:
(a) obtaining a culture supernatant from a culture of the bacteria;
(b) precipitating proteins in the supernatant with ammonium sulfate to produce a precipitate;
(c) suspending the precipitate in a buffer, 5 mM 20 mM Tris(hydroxy)methyl aminomethane hydrochloride, pH 7.0–8.0, to form a suspension;
(d) dialyzing the suspension against the buffer to form a solution;
(e) applying the solution to an affinity column in which P1 glycoprotein is bound to a solid phase; and
(f) eluting from the solid phase any material which bound to the P1 glycoprotein, thereby producing the substantially pure peptide or protein.

Also provided is a substantially pure antigenic peptide or protein related to Shiga-like toxin IIvh obtained from a culture of bacteria capable of producing Shiga-like toxin IIvh or a protein or peptide related thereto, the substantially pure antigenic protein or peptide obtained by a method comprising:
(a) obtaining a culture supernatant from a culture of the bacteria;
(b) applying the supernatant to an affinity column in which P1 glycoprotein is bound to a solid phase support; and
(c) eluting from the support any material which bound to the P1 glycoprotein, thereby producing the substantially pure peptide or protein.

In another embodiment, the present invention provides a substantially pure antigenic peptide or protein related to Shiga-like toxin IIvh obtained from a culture of bacteria capable of producing Shiga-like toxin IIvh or a protein or peptide related thereto, the substantially pure antigenic protein or peptide obtained by a method comprising:
(a) obtaining a culture supernatant from a culture of the bacteria;
(b) precipitating proteins in the supernatant with ammonium sulfate to produce a precipitate;
(c) suspending the precipitate in a buffer, preferably 5 mM–20 mM Tris(hydroxy)methyl aminomethane hydrochloride, pH 7.0–8.0, to form a suspension;
(d) dialyzing the suspension against the buffer to form a solution;
(e) applying the solution to an affinity column in which P1 glycoprotein is bound to a solid phase; and
(f) eluting from the solid phase any material which bound to the P1 glycoprotein,
thereby producing the substantially pure peptide or protein.

For producing the substantially pure antigenic protein or peptide related to Shiga-like toxin II, IIvp or IIvh, as above, the bacteria are preferably of the species *E. coli*. For producing the peptide or protein related to Shiga-like toxin IIvh, the *E. coli* are preferably of the strain DH5α(B2F1). For producing the peptide or protein related to Shiga-like toxin IIvp, the *E. coli* are preferably of the strain HB101 (pDLW5).

In all of the above, the bacterial cell pellet is preferably produced by centrifuging or filtering the bacteria.

In another embodiment, the present invention is directed to a substantially pure antigenic peptide or protein related to the Shiga-like toxin II capable of stimulating the production of an antibody which reacts with Shiga toxin and Shiga-like toxin I.

Also provided is an antibody specific for an epitope of the protein or peptide related to Shiga-like toxin II which protein or peptide is capable of stimulating the production of an antibody which reacts with Shiga toxin and Shiga-like toxin I, said antibody reacting with Shiga toxin and Shiga-like toxin I. The above antibody may be polyclonal or monoclonal.

The present invention is further directed to a subunit vaccine formulation capable of inducing immunity against a Shiga toxin, comprising:
(a) an immunogen which comprises an immunogenically effective amount of the peptide or protein related to Shiga toxin, as described above; and
(b) a pharmaceutically acceptable carrier.

Also provided is a subunit vaccine formulation capable of inducing immunity against Shiga-like toxin I, comprising:
(a) an immunogen which comprises an immunogenically effective amount of the peptide or protein related to Shiga-like toxin II, as described above; and
(b) a pharmaceutically acceptable carrier.

Also included is a subunit vaccine formulation capable of inducing immunity against a Shiga-like toxin II, comprising:
(a) an immunogen which comprises an immunogenically effective amount of the peptide or protein related to Shiga-like toxin II, as described above; and
(b) a pharmaceutically acceptable carrier.

In another embodiment is provided a subunit vaccine formulation capable of inducing immunity against Shiga-like toxin IIvp, comprising:
(a) an immunogen which comprises an immunogenically effective amount of the peptide or protein related to Shiga-like toxin IIvp, as described above; and
(b) a pharmaceutically acceptable carrier.

Also provided is a subunit vaccine formulation capable of inducing immunity against Shiga-like toxin IIvh, comprising:
(a) an immunogen which comprises an immunogenically effective amount of the peptide or protein related to Shiga-like toxin IIvh; and
(b) a pharmaceutically acceptable carrier.

In another embodiment, the present invention provides a method for removing Shiga toxin, Shiga-like toxin I, Shiga-like toxin II, Shiga-like toxin IIvh or Shiga-like toxin IIvp from a biological sample, the method comprising:
(a) contacting the sample with a capture reagent capable of binding to the toxin to form a complex between the capture reagent and any of the toxin present in the sample; and
(b) removing the complex from the sample, thereby removing the toxin.

In the above method, the capture reagent is preferably hydatid cyst material, P1 glycoprotein or an antibody specific for the toxin, and is preferably attached to a solid phase support. The sample may be a cell culture supernatant, preferably a bacterial culture. When the toxin is a shiga toxin, the culture is preferably a Shigella culture, most preferably of the species *Shigella dysenteriae* type I. When the toxin is Shiga-like toxin I, II or a variant thereof, the bacterial culture is preferably an *Escherichia coli* culture, such as an *Escherichia coli* 0157:H7 culture.

In the above method for removing a toxin, the sample is preferably a body fluid, which is most preferably selected from the group consisting of saliva, nasal secretion, mucus, blood, pleural fluid, peritoneal fluid, cerebrospinal fluid, and gastric aspirate, stool or small or large bowel contents.

Also provided herein is a method for detecting Shiga toxin in a sample, comprising:
(a) contacting the sample suspected of containing the toxin with a solid phase support to which is bound a toxin capture reagent capable of binding the toxin under conditions wherein the toxin binds to the capture reagent;
(b) contacting the support to which the toxin has bound with a first antibody capable of specifically binding to the toxin, wherein the binding of the antibody to the support indicates the presence of the toxin bound to the support; and
(c) detecting the presence or absence of the antibody bound to the support,
thereby detecting the toxin.

The capture reagent is preferably selected from the group consisting of hydatid cyst material, P1 glycoprotein, a monoclonal antibody specific for an epitope of Shiga toxin and the glycolipid Gb3.

In another embodiment, the present invention is directed to a method for detecting Shiga-like toxin I in a sample, comprising:
(a) contacting the sample suspected of containing the toxin with a solid phase support to which is bound a toxin capture reagent capable of binding the toxin under conditions wherein the toxin binds to the capture reagent;
(b) contacting the support to which the toxin has bound with a first antibody capable of specifically binding to the toxin, wherein the binding of the antibody to the support indicates the presence of the toxin bound to the support; and
(c) detecting the presence or absence of the antibody bound to the support,
thereby detecting the toxin.

In the method for detecting Shiga-like toxin I, the capture reagent is preferably selected from the group consisting of hydatid cyst material, P1 glycoprotein, a monoclonal antibody specific for an epitope of Shiga-like toxin I, or the glycolipid Gb3.

Also provide is a method for detecting Shiga-like toxin II in a sample, comprising:
(a) contacting the sample suspected of containing the toxin with a solid phase support to which is bound a toxin capture reagent capable of binding the toxin under conditions wherein the toxin binds to the capture reagent;
(b) contacting the support to which the toxin has bound with a first antibody capable of specifically binding to the toxin, wherein the binding of the antibody to the support indicates the presence of the toxin bound to the support; and
(c) detecting the presence or absence of the antibody bound to the support,
thereby detecting the toxin.

In the method for detecting Shiga-like toxin II, the capture reagent is preferably selected from the group consisting of hydatid cyst material, P1 glycoprotein, a monoclonal antibody specific for an epitope of Shiga-like toxin II, and the glycolipid Gb3.

The above method can also be used to detect Shiga-like toxin IIvh or IIvp in a sample. In this method the capture reagent is selected from the group consisting of hydatid cyst material, P1 glycoprotein, and a monoclonal antibody specific for an epitope of Shiga-like toxin IIvh or IIvp. For detecting Shiga-like toxin IIvp the capture reagent may also be the glycolipid Gb4.

In the above detection method, the sample is preferably a tissue sample or a body fluid. The first antibody may be a polyclonal or monoclonal antibody. The detecting step (c) is preferably performed by:
 i. contacting the solid surface to which the first antibody has bound with a second detectably labeled antibody capable of binding to the first antibody
 ii. detecting the presence or absence the detectable label bound to the solid surface.

The second antibody may be a polyclonal or monoclonal antibody. The detectable label is preferably an enzyme.

The present invention also includes a kit for detecting Shiga toxin, or Shiga-like toxins I or II, or Shiga-like toxin II variants, according to the method described above, the kit being compartmentalized to receive in close confinement therein one or more containers, the kit comprising:
(a) a first container means containing P1 glycoprotein, preferably bound to a solid phase support;
(b) a second container means containing a first antibody capable of binding to the respective toxin.

In the above kit the first antibody may be a polyclonal or monoclonal antibody.

In another embodiment, the above kit further comprises
(c) a third container means containing a detectably labeled second antibody, polyclonal or monoclonal, capable of binding the first antibody.

The second antibody is preferably detectably labelled with an enzyme.

In another embodiment wherein the second antibody is labeled with an enzyme, the above kit further comprises
(d) a fourth container means containing a substrate for the enzyme.

The present invention is further directed to a method for treating Shigellosis, hemolytic uremic syndrome or hemorrhagic colitis in a host, preferably a human, comprising administering to the host an effective amount of P1 glycoprotein.

Also included is a method for treating porcine edema (edema disease of swine) in an animal host, comprising administering to the host an effective amount of P1 glycoprotein.

4. DESCRIPTION OF THE FIGURES

FIG. 1 shows the reactivity of Shiga toxin (ST) to preparations of hydatid cyst protein with varying amounts of the P1gp. $^{125}$I-labelled ST was preincubated with various concentrations of three preparations of hydatid cyst protein of differing specific seroreactivity with P1 blood group antigen. Binding to HeLa cells was then determined and is expressed as percentage of controls incubated without prior exposure to hydatid cyst protein. Δ=crude hydatid cyst protein; ○ 10–20% ethanol precipitate; □=30–40% ethanol precipitate (Morgan, supra).

FIG. 2 compares $^3$H-leucine incorporation into HeLa cells (□) with the binding of $^{125}$I-ST to HeLa cells (○) in the presence of increasing concentrations of crude hydatid cyst protein.

FIGS. 3A and 3B show SDS-PAGE of ST after small scale purification. ST was purified in one step from the crude cell lysate of a 500 ml culture of *Shigella dysenteriae* 60R by the P1gp receptor analogue affinity chromatography (RAAC) method as described in Section 6.1.2, infra. SDS-PAGE was performed on the crude cell lysate (3A) and the purified toxin after MgCl$_2$ elution and dialysis (3B). The molecular weight markers on the left (Bio Rad) were: 92.5 kDa (phosphorylase B); 66.2 kDa (bovine serum albumin); 45 kDa (ovalbumin); 31 kDa (carbonic anhydrase); 21 kDa (soybean trypsin inhibitor); 14.4 kDa (lysozyme).

FIGS. 4A and 4B show SDS-PAGE and Western blot analysis of Shiga family toxins purified by the P1gp RAAC method.
Panel 4A: SDS-PAGE of P1gp purified ST (Lane 1), P1gp purified *E. coli* 0157:H7 supernatant (Lane 2), and P1gp purified supernatant from *E. coli* C600 containing the 933W phage (SLT-II) (Lane 3).
Panel 4B: Western blot of Lanes 1, 2 and 3 incubated with polyclonal rabbit antiserum to ST (molecular weight markers as in FIG. 3).

Figure 7:
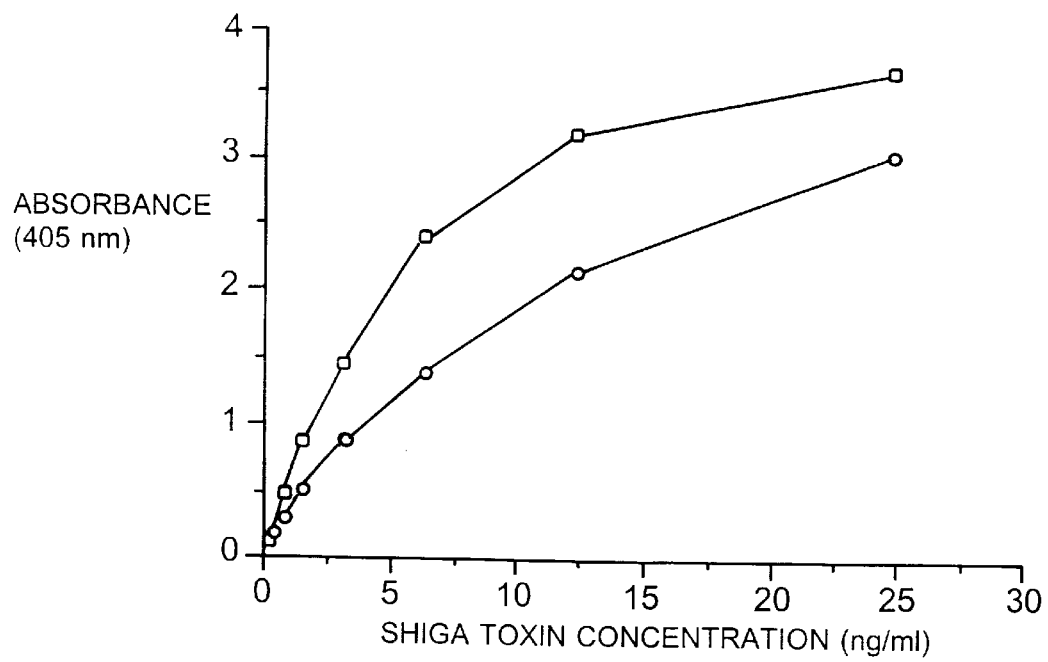

FIG. 7 shows the detection of ST by ELISA. ELISA plates were coated with either crude hydatid cyst material (○) or mAb to the B subunit of ST (□) and reacted with ST in a sandwich ELISA using polyclonal rabbit antisera as the detecting antibody. Changes in absorption (A$_{405}$) are shown with increasing concentrations of ST.

Figure 8:
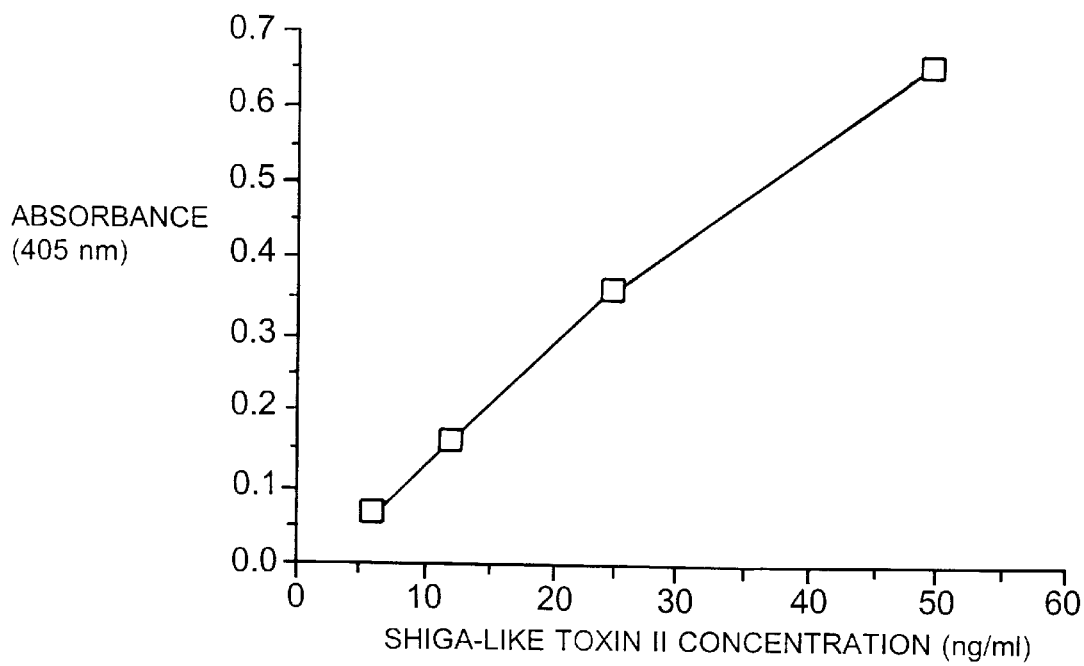

FIG. 8 shows the detection of SLT-II by ELISA. ELISA plates were coated with crude hydatid cyst material and reacted with SLT-II in a sandwich ELISA using polyclonal mouse antisera as the detecting antibody. Changes in A$_{405}$ are shown with increasing concentrations of SLT-II.

Figure 9:
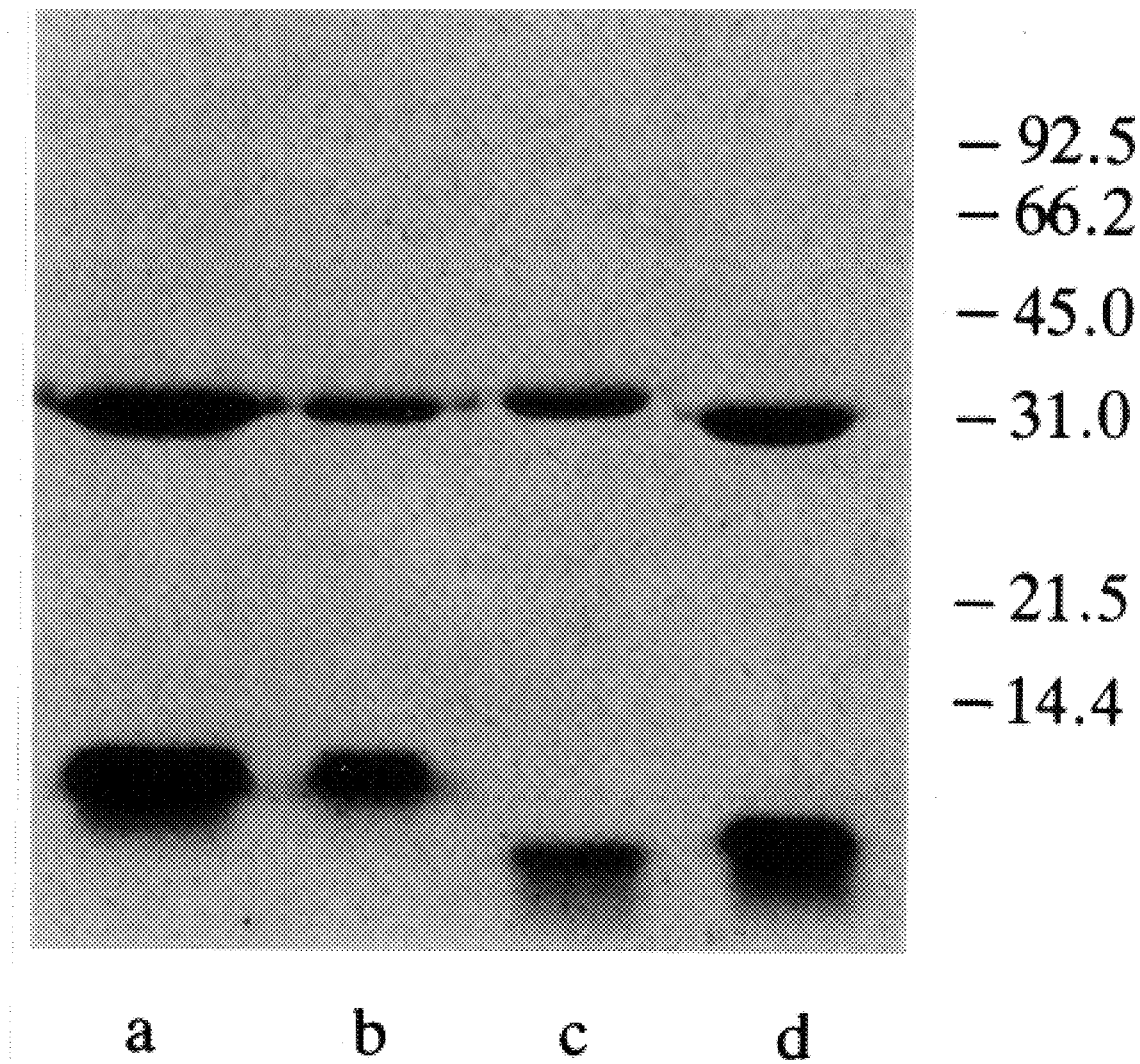

FIG. 9 is a gel pattern showing SDS-PAGE analysis of SLT-II and variants. SLT-IIvh (Lane A), SLT-II (Lane B), SLT-IIvp (Lane C) and ST (Lane D) which had been purified using hydatid cyst material were run on 15% SDS-PAGE and the gel stained with Coomassie Blue. Molecular weight markers were as described above.

FIGS. 10A and 10B are graphs showing cytotoxicity of ST (□), SLT-IIvp (○) and SLT-IIvh (Δ) measured as reduction of $^3$H-leucine incorporation in HeLa 229 cells (Panel 10A) and Vero cells (Panel 10B).

Figure 11A:
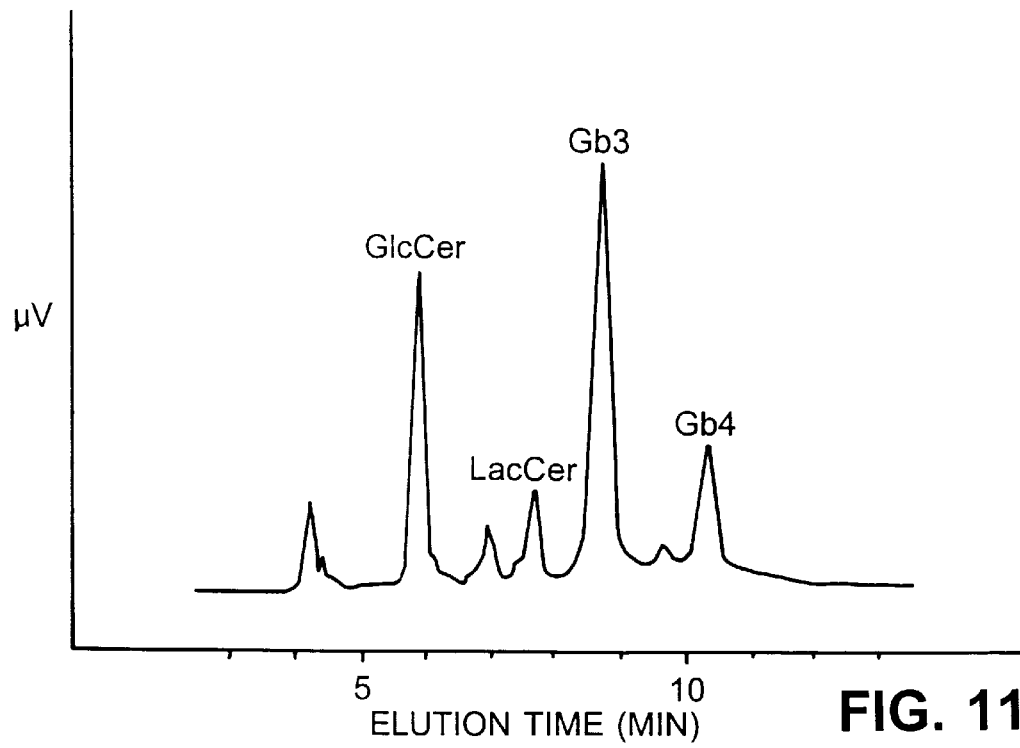
Figure 11B:
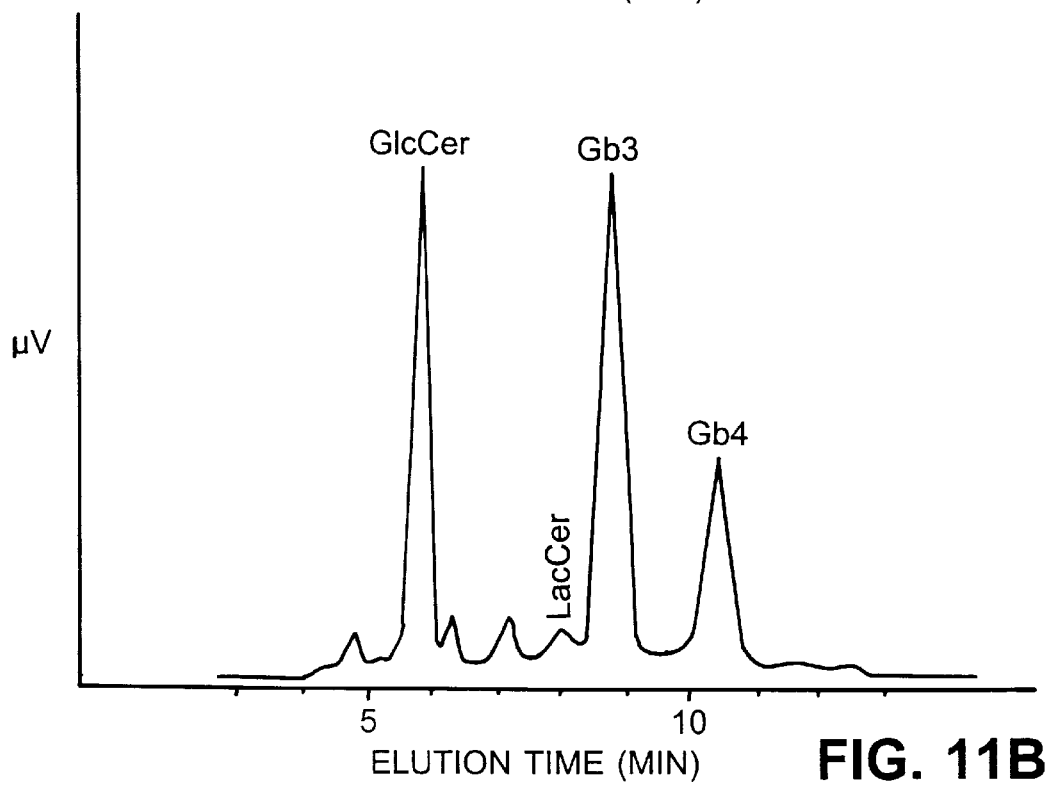

FIGS. 11A and 11B show chromatograms from HPLC analysis of the glycolipid composition of Vero cells (Panel 4A) and HeLa 229 cells (Panel 4B).

FIGS. 12A–12D are a set of graphs showing the quantitation of four toxins using four different capture systems. The capture reagents were:

Panel 12A—hydatid cyst material; Panel 12B—monoclonal antibody 4D1; Panel 12C—glycolipid Gb3; and Panel 12D—glycolipid Gb4. The toxins detected (by ELISA) were: ST (■), SLT-II (●), SLT-IIvh (○) and SLT-IIvp (Δ).

5. DETAILED DESCRIPTION OF THE INVENTION

The present invention relates to a substantially pure antigenic or peptide protein related to Shiga toxin (ST) or Shiga-like toxins I or II (SLT-II, SLT-II) or SLT-II variants. The term "related to" refers to a peptide or protein that have the same biological activity as ST, SLT-I, SLT-II or SLT-II variants which have been altered by the substitution of one or more amino acid residues within the sequence by another amino acid of a similar polarity which acts as a functional equivalent thus resulting in a silent alteration.

Provided herein are antibodies to SLT-II, which may or may not cross-react with ST and SLT-I.

ST, SLT-I, SLT-II and SLT-II variants are obtained by the methods of the present invention and may be used in subunit vaccine formulations.

The invention is also directed to methods for removing ST, SLT-I, SLT-II or SLT-II variants from a sample, preferably a biological fluid, comprising binding the toxin to P1 glycoprotein (P1gp) and removing the resulting toxin-P1gp complex from the sample.

In one embodiment, the method of the present invention may be used to obtain substantially pure ST, SLT-I, SLT-II or an SLT-II variant for use in a vaccine formulation by obtaining the toxin in pure form from a culture supernatant. In another embodiment, the method of the invention may be used to remove the toxin from a biological sample, preferably a body fluid such as saliva, nasal secretion, mucus, blood, pleural fluid, peritoneal fluid, cerebrospinal fluid, or a gastric aspirate.

The present invention is further directed to methods and kits for detecting ST, SLT-I, SLT-II or an SLT-II variant using a sandwich ELISA. Specifically, a solid phase matrix or carrier with a bound ligand for the toxin, preferably P1gp, is employed to form a complex with the toxin molecules, resulting in the toxin being bound to the carrier. The toxin is then detected using: a first antibody specific for the toxin (i.e., ST, SLT-I, SLT-II, or an SLT-II variant), followed by a detectably labeled reporter molecule, preferably a labelled second antibody capable of reacting with the first antibody. Such methods and kits may be useful for the detection of Shigellosis or disorders associated with the expression of SLT's, including hemolytic uremic syndrome or hemorrhagic colitis.

The present invention also provides methods for treating disorders associated with the expression of ST, SLT-I, SLT-II or SLT-II variants using the P1gp. Since P1gp specifically binds to the above toxins, it may be used to neutralize and prevent the in vivo actions of the toxins on erythrocytes, as described in Section 2, supra, or on other body tissues.

5.1 ISOLATION AND PURIFICATION OF SHIGA AND SHIGA-LIKE TOXINS I AND II

ST, SLT-I, SLT-II or SLT-II variants may be obtained in substantially pure form from a bacterial culture by a method comprising the following steps:

(a) concentrating the bacterial cells in the culture to produce a cell pellet and a culture supernatant; and (b) applying the supernatant, either in crude form or, preferably, after enriching the proteins by ammonium sulfate precipitation, to an affinity column to which is bound a ligand which can selectively bind to the toxin, allowing any toxin to bind to the ligand, and eluting the bound toxin from the column, thereby producing the toxin in substantially pure form. Preferred ligands are hydatid cyst material, or more preferably, P1gp. In another embodiment, an antibody specific for an epitope of the toxin molecule, as described herein, may be used as the ligand for purification.

The bacterial cells may be concentrated by any method known in the art, such as centrifugation or filtration. In a preferred embodiment, the cells in the cell pellet are lysed and the lysate is applied to an affinity column. The cells can be physically disrupted by methods well-known in the art, including but not limited to, sonication, grinding or homogenization.

ST may be obtained from a cell culture of Shigella, preferably from the species Shigella dysenteriae. As will be appreciated by one of ordinary skill in the art, ST, as well as the SLT's discussed below, can be obtained from any organism into which a gene encoding the toxin protein (or a peptide portion thereof) has been cloned. Thus, even though is generally exemplified as being obtained from a culture of Shigella, the source of ST is not intended to be so limited. Similarly, the sources of SLT-I, SLT-II or SLT-II variants is not intended to be limited to the bacterial strains exemplified herein.

SLT-I or SLT-II may be obtained from a culture of bacteria such as *E. coli*, Vibrio, Salmonella, or Campylobacter, preferably from *E. coli*. In a preferred embodiment, SLT-I is obtained from a culture of *E. coli* 0157:H7. As disclosed in Section 2.2, supra, the culture supernatants contain mainly SLT-II whereas the cell lysates contain mainly SLT-I.

SLT-I may be obtained from *E. coli* C600 transformed with bacteriophage 933J. SLT-II may also be obtained from *E. coli* C600 transformed with bacteriophage 933W. In yet another embodiment, SLT-I and SLT-II may be isolated a body fluid of a subject infected with a bacterial strains producing the toxin. For producing SLT-IIvp, preferred bacteria are of the strain *E. coli* HB101(pDLW5) (Weinstein et al., supra). For producing SLT-IIvh, preferred bacteria are of the strain *E. coli* DH5α(B2F1) (Samuel, J. E. et al., Infect. Immun. 58:611–618 (1990)).

ST, SLT-I, SLT-II and SLT-II variants may be isolated from a small scale cell culture of up to about 500 ml of culture or a large scale cell culture, of up to at least 20 liters of culture. Isolation of the toxin can render the culture devoid of the toxins.

As disclosed in Keusch et al., *Methods In Enzymology* 165:152–162, 399–401 (1988), herein incorporated by reference in its entirety), for production of the toxin proteins and peptides of the present invention, the composition of the culture medium is important. Preferably, the medium has a lower ionic concentration than standard culture media. The ion concentrations of standard bacterial culture media result in repression of the genes encoding the toxins. The concentration of $Fe^{3+}$ ions is particularly important. Most media have $Fe^{3+}$ concentrations of about 1 μM. A preferred $Fe^{3+}$ concentration for producing the toxins of the present invention is about 0.15 μM. This concentration may be achieved by adding iron chelating substances, well-known in the art, to a conventional medium. Alternatively, some commercial media such as modified syncase broth (MSB) are formulated such that iron (and other components) are added to the basal medium prior to use. By using MSB without adding additional iron, the preferred concentration of $Fe^{3+}$ can be achieved (Donohue-Rolfe et al., *J. Exp. Med.* 160:1767–1781 (1984)). MSB contains (per liter): 10 g. casamino acids, 5 g. $Na_2HPO_4$, 5 g. $K_2HPO_4$, 1.18 g. $NH_4Cl$, 0.089 g. $Na_2SO_4$, 0.042 g. $MgCl_2$II6H2O, and 0.004 g. $MnCl_2II4H_2O$. To 500 ml of this stock is added 5 ml of 20% (w/v) glucose and 0.4% tryptophan.

It is also important that the cultures be maximally oxygenated, preferably by aeration and vigorous agitation, preferably at about 300 rpm on a rotatory shaker, for maximum toxin production. Solid or semisolid media should be avoided. Thus, methods described by others (see, for example, Healey (U.S. Pat. No. 4,981,685) using solid media are inappropriate for the present invention.

The toxins of the present invention are generally produced by bacteria as periplasmic proteins which are released into the medium primarily upon death and lysis of the organism. Thus, for those embodiments wherein the toxins are extracted from bacterial cell pellets, it is preferable to obtain the periplasmic proteins relatively free of contamination with cytoplasmic proteins. This can be done by osmotic shock lysis. A preferred method is to extract the bacterial pellet with the detergent-like antibiotic, polymyxin B. For example, the bacterial cell pellet is incubated for about 2 min at 4° C. in a 2 mg/ml solution of polymyxin B in 25 mM phosphate buffer, pH 7.3, containing 0.14M NaCl. This releases over 90% of the total toxin (cytotoxic activity) contained in a French pressure cell lysate, with less than 5% of the cytoplasmic proteins.

It is also possible, using recombinant methods well-known in the art, to engineer bacterial strains which produce extracellular toxins rather than periplasmic toxins. Such toxins are then obtained from the culture supernatants using conventional methods and purified as described herein.

In a preferred embodiment, ST, SLT-I, SLT-II or an SLT-II variant may be partially purified from a large or small scale culture before applying to an affinity column. In such a method, a culture supernatant or a cell lysate is first precipitated with ammonium sulfate to enrich the proteins. The precipitate is suspended in a buffered solution, preferably 5–20 mM Tris(hydroxymethyl)aminomethane hydrochloride, pH 7.0–8.0 and dialyzed against the same buffer. The dialysate is loaded onto an affinity column in which the solid phase carrier, such as Sepharose 4B has bound to it the ligand for the toxin, preferably P1gp.

In another embodiment the toxin may be further purified after ammonium sulfate precipitation and prior to affinity chromatography by applying the dialysate to, for example, a Blue Sepharose column or by subjecting the dialysate to chromatofocusing.

5.2. PRODUCTION OF ANTIBODIES TO SHIGA TOXIN AND SHIGA-LIKE TOXINS I AND II

The term "antibody" as used herein is meant to include polyclonal antibodies, monoclonal antibodies (mAbs), anti-idiotypic (anti-Id) antibodies, humanized or chimeric antibodies, and single chain antibodies (see below).

The present invention provides antibodies, polyclonal or monoclonal, which are specific for ST, SLT-I, SLT-II or an SLT-II variant.

Various procedures known in the art may be used for the production of polyclonal antibodies to the toxin. A host animal is immunized by injection of toxin-containing material, or a semi-purified or purified toxin preparation, or a with a synthetic protein, or peptide fragment corresponding to the toxin molecule. Host animals include, but are not limited to. rabbits, mice, rats, horses, goats, sheep, etc. Any of a number of immunological adjuvants, well-known in the art (see, for example, Gregoriades, G. et al., *Immunological Adjuvants and Vaccines,* Plenum Press, New York, 1989), may be used to increase the antibody response to the toxin. Selection of the adjuvant depends on the animal used, as is well-known in the art. Examples of useful adjuvants include , Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and the bacteria *Propionibacterium acnes* (formerly *Corynebacterium parvum*) or bacterial products or their synthetic analogues, such as muramyl dipeptide-derived synthetic peptide adjuvants (e.g., murabutide) which ahve adjuvant activity.

A monoclonal antibody to ST, SLT-I, SLT-II or an SLT-II variant can be prepared using any technique which provides for the production of antibody molecules by continuous cell lines in culture. These include but are not limited to the hybridoma technique originally described by Kohler and Milstein (1975, Nature 246:495–97), and the more recent human B cell hybridoma technique (Kozbor et al., 1983, Immunology Today 4:72) and EBV-hybridoma technique (Cole et al., 1985, *Monoclonal Antibodies and Cancer Therapy,* Alan R. Liss, Inc., pp. 77–96). For an overview of monoclonal antibody technology, see, for example, Hartlow, E. et al., *Antibodies: A Laboratory Manual,* Cold Spring Harbor Laboratory Press, Cold Spring Harbor, N.Y., 1988). Human mAbs may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Such antibodies may be of any immunoglobulin class including IgG, IgM, IgE, IgA and any subclass thereof. The hybridoma producing the mAbs of this invention may be cultivated in vitro or in vivo.

Antibody molecules may be purified by known techniques, such as immunoabsorption or immunoaffinity chromatography, high performance liquid chromatography (HPLC), or a combination thereof, etc.

The term "antibody" is also meant to include both intact molecules as well as fragments thereof, such as, for example, Fab, $F(ab')_2$, and Fv, which are capable of binding antigen. Fab and $F(ab')_2$ fragments lack the Fc fragment of intact antibody, clear more rapidly from the circulation, and may have less non-specific tissue binding than an intact antibody (Wahl et al., *J. Nucl. Med.* 24:316–325 (1983)). It will be appreciated that Fab and $F(ab')_2$ and other fragments of the antibodies useful in the present invention may be used for the detection and quantitation of the toxin molecules according to the methods disclosed herein for intact antibody molecules. Such fragments are typically produced by proteolytic cleavage, using enzymes such as papain (to produce Fab fragments) or pepsin (to produce $F(ab')_2$ fragments).

In another embodiment, the antibody is a chimeric antibody, preferably a mouse-human chimeric antibody, wherein the heavy and light chain variable regions are derived from a murine mAb and the constant regions are of human origin. The chimeric antibodies of this invention have both the toxin-recognizing specificity of the mouse mAb and the biological properties of human antibodies, which include resistance to clearance in the human and lower immunogenicity for humans, allowing multiple treatments. Method for producing chimeric antibody molecules are disclosed, for example, in Gorman et al., PCT Pub.WO9206193 (Apr. 16, 1992); Cabilly et al., U.S. Pat. No. 4,816,567 (Mar. 28, 1989) and Eur. Patent Pub. EP125023 (Nov. 14, 1984); Taniguchi et al., EPO Pub. EP171496 (Feb. 19, 1986); Morrison et al., EPO Pub. EP173494 (Mar. 5, 1986); Neuberger et al., PCT Pub. WO8601533 (Mar. 13, 1986); Kudo et al., EPO Pub. EP184187 (Jun. 11, 1986); Robinson et al., PCT Pub. WO 8702671 (May 7, 1987); Boulianne et al., *Nature* 312:643–646 (1984); Morrison, *Science,* 229:1202–1207 (1985); Neuberger et al., *Nature* 314:268–270 (1985); Takeda et al., *Nature* 314:452–454 (1985); Oi et al., *BioTechniques* 4:214 (1986); and Liu et al., *Proc. Natl. Acad. Sci. USA* 84:3439–3443 (1987).

For human therapeutic purposes, mAbs or chimeric antibodies can be "humanized" by producing human constant region chimeras, where even parts of the variable regions, in particular the conserved or framework regions of the antigen-binding domain, are of human origin, and only the hypervariable regions are non-human. See for example, UK Patent Publication GB 2188638A); Harris et al., PCT Pub. WO 9204381 (Mar. 19, 1992); Riechmann et al., *Nature* 332:323–327 (1988).

In yet another embodiment, the antibody is a single chain antibody formed by linking the heavy and light chain fragment of the Fv region via an amino acid bridge, resulting in a single chain polypeptide (Bird, 1988, Science 242:423–426; Huston et al, 1988, Proc.Natl.Acad.Sci. USA 85:5879–5883: and Ward et al, 1989, Nature 34:544–546).

The specificity and reactivity of antibodies generated may be determined using procedures well-known in the art. These include but are not limited to enzyme linked immunosorbent assay (ELISA) (Voller, A. et al., *Bull. WHO* 53:55–65 (1976); Voller, A. et al., *J. Clin. Pathol.* 31:507–520 (1978); Butler, J. E., Meth. Enzymol. 73:482–523 (1981); Maggio, E. (ed.), *Enzyme Immunoassay,* CRC Press, Boca Raton, Fla., 1980; Ishikawa, E. et al. (eds.) *Enzyme Immunoassay,* Kgaku Shoin, Tokyo, 1981) radioimmunoassay (RIA) (Weintraub, B., *Principles of Radioimmunoassays,* Seventh Training Course on Radioligand Assay Techniques, The Endocrine Society, March, 1986, pp. 1–5, 46–49 and 68–78), gel diffusion precipitin reaction assay, and Western Blot analysis.

5.3. SUBUNIT VACCINE FORMULATIONS

ST, SLT-I, SLT-II or SLT-II variant proteins or peptides may be used as immunogens in subunit vaccine formulations. For human immunotherapy, if attenuated live organisms are not used, it is generally required that vaccine antigens be substantially purified, as described herein for ST and the various SLTs. Crude preparations, such as those disclosed in Healey (supra) are unacceptable today for human vaccine formulations. The toxin protein or peptide may be adjusted to an appropriate concentration and formulated with any suitable vaccine adjuvant and packaged for use. Suitable adjuvants include, but are not limited to: mineral gels, e.g., aluminum hydroxide; surface active substances such as lysolecithin, pluronic polyols; polyanions; peptides, and oil emulsions. The ST, SLT-I, SLT-II or variants thereof may also be conjugated to polysaccharides and/or polymers for use in a vaccine formulation.

The toxin protein or peptide may also be incorporated into liposomes (see, for example, Michalek, S. M. et al., Liposomes as Oral Adjuvants, *Curr. Top. Microbiol. Immunol.* 146:51–58 (1989)), pharmaceutical compositions in which the active ingredient is contained either dispersed or variously present in corpuscles consisting of aqueous concentric layers adherent to lipidic layers. The toxin protein or peptide may be present both in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

In instances where the peptide of ST, SLT-I, SLT-II or variant is too small to be immunogenic on its own (i.e., a hapten) the peptide may be covalently bound to a. carrier or immunogenic molecule and the peptide-carrier complex may be formulated for use as a vaccine; for example, a large protein such as a heterologous serum albumin will confer immunogenicity to a hapten coupled to it.

5.4. DETECTION OF ST, SLT-I, SLT-II OR AN SLT-II VARIANT

ST, SLT-I, SLT-II or an SLT-II variant may be detected in immunoassays according to the present invention, using antibodies provided herein. The immunoassay method preferably comprises contacting a sample suspected of containing the toxin with a "capture ligand" capable of binding the toxin. A preferred ligand for the toxin is the P1gp. Other useful ligands include a capture antibody which is specific for the toxin, preferably an antibody different from the antibody being used as the detecting antibody, or a glycolipid such as Gb3 or Gb4 (see Examples, below). The ligand is preferably attached to a solid phase support. This results in the formation of a complex between the ligand, such as P1gp and the toxin.

By "solid phase support" is intended any support capable of binding a capture ligand, preferably the P1gp. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to a protein or glycoprotein, glycolipid or saccharide. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The capture ligand, preferably P1gp may be attached to the carrier or support using procedures described in the art. After washing, antibody capable of forming an antigen-antibody complex with the toxin is added. The solid phase complex is then washed, and the presence or absence of the toxin is determined by detecting the presence of the detection antibody. For example, the detection antibody may be labelled, or detected by means of a second, detectably labelled reporter molecule which reacts with the detection antibody forming an antigen-antibody-antibody sandwich. In a preferred embodiment, the detectable label is an enzyme, and the presence of the sandwich is confirmed by adding a substrate for the enzyme, which upon hydrolysis produces an analytically detectable change in the medium, for example using spectrophotometric, fluorometric or visual means. Generally preferred is a chromogenic substrate which yields a colored reaction product which is quantitatively evaluated by absorbance reading and compared against a standard.

The specificity of the antibody employed depends upon the identity of the toxin to be determined. Antibodies which are specific for only ST, SLT-I, SLT-II or an SLT-II variant and which do not react any of the other toxins of the present invention may be used. Alternatively, antibodies that react with more than one of the toxins may be used. As described above, the antibodies may be monoclonal or polyclonal, or a combination thereof.

The detectable label can be any molecule or moiety which is analytically detectable, such as a radioisotope, a chemiluminescent molecule, a fluorescent molecule, or a bioluminescent molecule. Particularly preferred, however, for simplicity and cost, are enzyme labels. Enzymes which can be used to detectably label the detection antibody or the reporter molecule include, but are not limited to, horseradish peroxidase, alkaline phosphatase, glucose-6-phosphate dehydrogenase, malate dehydrogenase, staphylococcal nuclease, delta-V-steroid isomerase, yeast alcohol dehydrogenase, alpha-glycerophosphate dehydrogenase, triose phosphate isomerase, , asparaginase, glucose oxidase, β-galactosidase, ribonuclease, urease, catalase, glucoamylase and acetylcholinesterase.

The skilled artisan will readily recognize the possible variations in the recognized ELISA or other immunoassay technique which can be adapted for use according to the present invention.

The method of the present invention is conveniently adaptable to use in kit form. The essential elements are:
(1) a capture reagent, preferably P1gp; and
(2) a detection antibody capable of binding to the toxin when it is bound by the capture reagent. In a preferred embodiment, the P1gp is attached to a solid support. The kit may further comprise a detectably labelled reagent, preferably an antibody, which is capable of binding to the detection antibody bound to the toxin. If the detectable label is an enzyme, the kit preferably includes a substrate for the enzyme. The kit may also conveniently include one or more buffers useful for binding, blocking or rinsing the reagents or solid support.

The method and kit described herein are useful for diagnosing diseases associated with the presence of ST, SLT-I, SLT-II or an SLT-II variant. These diseases include, but are not limited to, Shigellosis, hemolytic uremic syndrome including that associated with cancer (Acheson et al., *J. Clin Oncol.* 7:1943 (1989)), hemorrhagic colitis, thrombotic thrombocytopenic purpura, or porcine edema (edema disease of swine).

5.5. THERAPY OF DISORDERS CAUSED BY ST, SLT-I, SLT-II OR AN SLT-II VARIANT

The preferred animal subject of the present invention is a mammal. By the term "mammal" is meant an individual belonging to the class Mammalia. The invention is particularly useful in the treatment of human subjects.

By the term "treating" is intended the administering to subjects of a pharmaceutical composition according to this invention for purposes which may include prevention, amelioration, or cure of a disease or disorder associated with ST, SLT-I, SLT-II or an SLT-II variant.

The present invention includes a method for treating or preventing a disorder related to the expression of ST, SLT-I, SLT-II or an SLT-II variant, for example, shigellosis, hemolytic uremic syndrome, hemorrhagic colitis or porcine edema, which comprises providing to a subject in need of such treatment an effective amount of purified P1gp or a toxin-binding portion thereof. As described below (Section 6.2.1.) P1gp competitively inhibited the binding of ST to cultured cells. By inhibiting the binding of the toxin, such treatment may prevent or reduce the pathogenetic process of the disorder.

In a preferred embodiment, substantially pure P1gp, obtained using procedures well-known in the art is used to treat the disorder. Such procedures include, but are not limited to, gel exclusion chromatography, ion-exchange chromatography, gel electrophoresis, or affinity chromatography.

For such therapy, the compositions of the present invention can be formulated for a variety of modes of administration, either systemic or localized. Techniques and formulations generally may be found in *Remington's Pharmaceutical Sciences*, Meade Publishing Co., Easton, Pa., latest edition.

For example, administration may be by parenteral, subcutaneous, intravenous, intramuscular, intraperitoneal, transmucosal or transdermal routes. Alternatively, or concurrently, administration may be by the oral route. The dosage administered will be dependent upon the age, health, and weight of the recipient, kind of concurrent treatment, if any, frequency of treatment, and the nature of the effect desired.

In a preferred embodiment, the P1gp is coupled to beads, for example latex beads, for oral administration in a nonabsorbable form. Following administration, the P1gp-coated beads pass through the gastrointestinal system of the subject and bind any P1gp-binding toxin molecules, such as ST, SLT-I, SLT-II and variants thereof, present in the lumen. This capture of the toxin prevents its action on the intestinal mucosa or its absorption across the mucosa and its systemic spread (as occurs in hemoltyic uremic syndrome or edema disease). The P1gp-coupled beads, with toxin attached, are subsequently excreted in the stool.

For injection, the compositions of the invention are formulated in liquid solutions. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. For injection, the pharmaceutically active component, such as the P1gp is preferably dissolved in physiologically compatible buffers, such as Hank's or Ringer's. Aqueous injection suspensions that may contain substances which increase the viscosity of the suspension include, for example, sodium carboxymethyl cellulose, sorbitol, and/or dextran. Optionally, the suspension may also contain stabilizers. In addition, the compositions may be formulated solid form and redissolved or suspended immediately prior to use. Lyophilized forms are also included. For transmucosal or transdermal administration, penetrants appropriate to the barrier to be permeated are used in the formulation. Such penetrants are generally known in the art and include, for example, for transmucosal administration, bile salts and fusidic acid derivatives. In addition, detergents may be used to facilitate permeation. Transmucosal administration may be through nasal sprays, for example, or using suppositories. For oral administration, the compositions are formulated into conventional oral administration forms such as capsules, tablets, and tonics. compositions within the scope of this invention include all compositions wherein the P1gp or portion thereof is contained in an amount effective to achieve its intended purpose. While individual needs vary, determination of optimal ranges of effective amounts of each component is within the skill of the art. The dosages are based also on the known $LD_{50}$ of the toxins as well as the predicted total gut contents of the toxin. For example, values as low as 3 ng toxin/kg body weight have been observed with pigs, monkeys and rabbits. Thus, effective therapeutic dosages of the P1gp preparation are from about 0.001 to about 50 mg/kg body weight. Preferred dosages are from about 0.01 to 50 mg/kg body weight, more preferably, from about 0.1 to 50 mg/kg body weight.

6. EXAMPLE 1

PURIFICATION OF ST, SLT-I AND SLT-II BY RECEPTOR ANALOGUE AFFINITY CHROMATOGRAPHY WITH IMMOBILIZED P1 GLYCOPROTEIN AND THE PRODUCTION OF CROSS-REACTIVE MONOCLONAL ANTIBODIES

ST from *Shigella dysenteriae* type 1, strain 60R, was purified to homogeneity by a novel one step receptor analogue affinity chromatography (RAAC) method. The method is based on the binding affinity of Shiga family toxins for a specific disaccharide, Galα1→4Gal, which is also present in glycoproteins with P1 blood group seroreactivity produced by hydatid cysts from sheep infected with *Echinococcus granulosus*.

Having shown that cyst fluid P1gp bound ST on a solid phase, the present inventors made a P1gp affinity column by coupling P1-active substance to Sepharose-4B. This method allowed purification of ST in large quantities (5–10 mg/20 liter batch) with a consistently good yield (>80% of starting toxin). In addition, the same method enabled purification of SLT-I and SLT-II from *E. coli*.

A preparation enriched for SLT-II purified by RAAC was used to raise four mAbs which reacted with SLT-II in ELISA. Three of these four mAbs also reacted with ST, the first clear demonstration of cross-reactivity between these toxins. One mAb, 4D1, specific for the B subunit of SLT-II and ST, neutralized both toxins as measured in a cytotoxicity assay with HeLa cells.

Deposit of Hybridoma

A hybridoma producing monoclonal antibody 4D1 was deposited with the American Type Culture Collection (ATCC), 10801 University Boulevard, Manassas, Va. 20110, on Dec. 16, 1997 and was assigned accession number HB-12452.

Two mAbs recognized the A subunit of both SLT-II and ST by Western blot analysis but did not neutralize either toxin. In addition, one B subunit-specific mAb neutralized SLT-II alone, and a previously described mAb (Donohue-Rolfe et al., *J. Exp. Med.* 160:1767–1781 (1984)) specific for the ST B subunit was shown to be highly specific for ST and not reactive with SLT-II.

6.1. MATERIALS AND METHODS

6.1.1. P1 GLYCOPROTEIN

Crude and partially purified P1 glycoprotein (P1gp) from hydatid cysts were obtained from Drs. Marshall Lightowlers and Winifred Watkins, respectively. Crude HCF from fertile liver and lung cysts was obtained from sheep infected with *Echinococcus granulosus* and spun at slow speed to sediment the "sand." Clarified fluid (1400 ml) was dialyzed extensively against 25 volumes of distilled water with daily changes over 6 days and then lyophilized. Two partially purified P1gp preparations were prepared by Dr. Winifred Watkins (Morgan et al., supra). Crude HCF was diluted to 95:5 phenol:water (vol:vol) and separated into soluble and insoluble fractions. Partial purification of the 95% phenol-soluble P1gp was obtained by precipitation with 10–20% ethanol. The 95% phenol-insoluble material was harvested, solubilized in water, and a serologically more active P1gp fraction was obtained by precipitation in 30–40% ethanol.

The P1gp was coupled to cyanogen bromide-activated Sepharose 4B (Pharmacia, Uppsala, Sweden) using standard methods. 15 mg of the lyophilized partially purified P1gp yielded approximately 3 ml of hydrated gel.

6.1.2. PURIFICATION OF SHIGA TOXIN

6.1.2.1. SMALL SCALE PURIFICATION

*Shigella dysenteriae* type 1, strain 60R, was grown in 500 ml of syncase medium (Donohue-Rolfe et al., 1984, supra). After 16 hrs of growth, the culture was centrifuged at 11,950 x g at 4° C. for 10 minutes, and the supernatant was discarded. The pellet was resuspended in 250 ml of 10 mm Tris-HCl (pH 7.4) and re-centrifuged as above. The final cell pellet was suspended in 10 ml of 10 mM Tris-HCl (pH 7.4) and sonicated using a Branson Sonifier 450 (Danbury, Conn.) until the $A_{600}$ of the lysate had fallen to less than 10% of the original. The cell lysate was centrifuged (27,000 x g at 40° C.) for 15 minutes and the supernatant retained.

The supernatant was passed over a 0.5 ml P1gp affinity column in a 0.7×10 cm column (BioRad, Rockville, N.Y.) at a flow rate of 0.8 ml/hr. The column was then washed with 5 ml phosphate-buffered saline (PBS) (pH 7.4) followed by 5 ml 1M NaCl in 10 mM PBS (flow rate: 15 ml/hr), and finally eluted with 5 ml 4.5M $MgCl_2$ in 20 mM phosphate buffer (pH 7.5) at a flow rate of 15 ml/hr: The eluate was dialyzed extensively against 20 mM ammonium bicarbonate and then lyophilized.

6.1.2.2. LARGE SCALE PURIFICATION

*Shigella dysenteriae* type 1, strain 60R, was grown to stationary phase in 20 liters of syncase medium by overnight batch culture in a New Brunswick MF 128S fermenter (Edison, N.J.). The organisms were harvested on a Pellicon tangential flow membrane filtration system (Millipore, Bedford, Me.) and then washed twice in 10 mM Tris HCl (pH 7.4). Cells were lysed by passage through a cell press (SLM, Aminco, Urbana, Ill.) at 32,000 psi. The lysate was cleared by an initial centrifugation at 13,000 x g for 20 min, followed by centrifugation at 39,000 x g for 45 min. Proteins in the supernatant which precipitated at 30–60% saturation of ammonium sulfate were reconstituted in 10 mm Tris-HCl (pH 7.4), dialyzed extensively against the same buffer, and then loaded onto a column of Blue Sepharose (Pharmacia, Uppsala, Sweden) having a 400 ml bed volume. The column was washed extensively with 10 mm Tris-HCl (pH 7.4), and the crude toxin eluted with 0.5M NaCl in 10 mM Tris-HCl (pH 7.4) (Donohue-Rolfe et al., supra). Fractions containing toxin were determined by an ELISA method (Donohue-Rolfe et al. 1986, supra). The positive fractions were pooled, and a total volume of 60 ml was loaded onto a 3 ml P1gp-Sepharose column. Following washes with 10 mM PBS (pH 7.4) and 1M NaCl, purified toxin was eluted with 4.5M $MgCl_2$ and dialyzed extensively against 20 mm ammonium bicarbonate.

The concentration of protein eluted from the column was determined by a Bio Rad Assay (Bio Rad, Rockville Center, N.Y.) using bovine serum albumin (BSA) as a standard.

The toxins were characterized qualitatively by sodium dodecyl sulfate polyacrylamide gel electrophoresis (SDS-PAGE) using the procedure described by Donohue-Rolfe et al. (1984, supra) on slab gels (15×0.75 cm or 8×0.75 cm ).

6.1.3. PURIFICATION OF E. COLI SLT-I AND SLT-II

SLT-II was also prepared from E. coli, strain C600, containing the 933W phage (provided by Dr. H. Williams-Smith). The supernatant from an overnight growth in Luria-Bertani medium was brought to 70% saturation with ammonium sulfate. The precipitate was then solubilized, dialyzed and purified on the P1gp affinity column as above.

SLT-I and SLT-II were also prepared from E. coli 0157:H7 (from Dr. H. Williams-Smith) grown as above in 201 Luria-Bertani medium containing 0.1 mM 2,2' dipyridyl (Sigma Chemical Co., St. Louis, Mo.). A 70% ammonium sulfate precipitate of the culture supernatant was made. A cell lysate was also prepared using procedures described in Section 6.1.2.2., supra. The precipitate was dissolved in 10 mM Tris buffer (pH 7.4) and then dialyzed extensively against 10 mM Tris (pH 7.4) for at least 24 hours. The dialyzed ammonium sulfate precipitate was then applied to the P1gp affinity column, eluted and dialyzed as above.

The concentration of protein eluted from the column was determined as above and the toxins were characterized by SDS-PAGE as above.

6.1.4. PREPARATION OF MONOCLONAL ANTIBODIES

BALB/c mice were immunized with P1gp-purified supernatant ("antigen") from an overnight growth of E. coli 0157:H7. The antigen was incubated in a 1% formalin solution for 48 hours to inactivate any toxin, and then dialyzed against PBS (pH 7.4) prior to immunization. The protein used for immunization was largely SLT-II as defined by SDS-PAGE and Coomassie blue staining, although small amounts of SLT-I were present. The initial intraperitoneal immunization consisted of 50 pg protein in Freund's complete adjuvant and was followed 6 weeks later by a booster injection of 50 pg of protein in Freund's incomplete adjuvant. A final booster immunization (50 pg protein in saline) was given i.v. via the tail vein three days prior to sacrifice of the mice. Spleens was harvested under aseptic conditions, lymphocyte suspensions prepared, and the cells were fused to P3X63-Ag8.653 non-secreting mouse myeloma cells using standard procedures.

Hybridoma supernatants were tested by ELISA in 96 well plates (NUNC, Immuno-plate II, Neptune, N.J.) coated with ST or toxin purified from the supernatant of E. coli 157:H7 cultures. Positive cultures for binding with the toxin were cloned and the supernatants tested as before. Positive clones from this testing were subcloned and re-tested as above. The resulting hybridomas were transferred to 24-well plates and subsequently to 75 cm² flasks.

For in vivo maintenance of the hybridomas, BALB/c mice pretreated with 0.5 ml Pristane (Aldrich Chemical Co., Milwaukee, Wis.) 7 days earlier were injected i.p. with approximately $5 \times 10^6$ viable cells from four separate cell lines in 0.5 ml RPMI-1640 medium, and ascites fluid was tapped 10 days later. The immunoglobulin isotypes of the mAbs was performed with specific Ig-subtype alkaline phosphatase conjugates (Southern Biotechnology Associates Inc., Birmingham, Ala.).

Previously described antibodies include a mAb designated 4D3 specific for the ST B subunit and a rabbit polyclonal antibody to ST from the present inventors' laboratory (Donohue-Rolfe et al., 1984, supra).

To screen mAb binding, 96 well ELISA plates were coated with 100 μl/well of ST (1 pg/ml in PBS, pH 7.4) or SLT-II (0.1 pg/ml in PBS, pH 7.4) and incubated overnight at 4° C. The plates were blocked with 1% BSA for 60 minutes at room temperature and then washed extensively with PBS-Tween 20 (0.05%) prior to the addition of either hybridoma supernatants (40 μl/well) or dilutions of ascites fluid (1/2,000 to 1/16,000) diluted in PBS-Tween 20 (0.05%). The antibody preparations were allowed to incubate at room temperature for 2 hr. The plates were developed using an alkaline phosphatase-conjugated polyvalent goat anti-mouse Ig antibody (Sigma Chemical Co., St. Louis, Mo.) and Sigma 104 phosphate substrate. The absorption at 405 nm ($A_{405}$) was measured using an automated ELISA plate reader (Bio-Tek Instruments Inc., Winooski, Vt.).

6.1.5. WESTERN BLOTS

Toxins were covalently cross-linked with dimethylpimelimidate (Pierce Chemical Co., Rockford, Ill.) as previously described (Donohue-Rolfe et al., 1984, supra), and the resulting complexes were analyzed by SDS-PAGE on 15% gels. The separated complexes were electrophoretically blotted overnight at 100 mA onto Immobilon filters (Millipore, Bedford, Me.) in 25 mM Tris base, 192 mM glycine, and 20% methanol buffer (pH 8.3). The Immobilon filters were then blocked with a 5% solution of non-fat milk in TNT buffer (10 mM Tris, 159 mM NaCl, 0.05% Tween-20, pH 8.0) for 1 hr, washed with TNT buffer and incubated with either a polyclonal immune mouse antiserum (1:1000) from the donor animal used in the fusion, or with ascites fluid (1:1000) for 1 hr. Filters were then extensively washed with TNT buffer and incubated with the alkaline phosphatase conjugated goat anti-mouse Ig reagent (Promega Protoblot, Promega Biotec, Madison, Wis.) for 30 minutes, washed again with TNT buffer and then developed by adding 10 ml of buffer (100 mm Tris-HCl, 100 mM NaCl, 5 mm $MgCl_2$, pH 9.5) containing 66 μl nitroblue tetrazolium (50 mg/ml in 70% dimethylformamide), and 33 μl substrate (5-bromo-4-chloro-3-indolyl phosphate (BCIP), 50 mg/ml in dimethylformamide).

6.1.6. CYTOTOXICITY AND TOXIN NEUTRALIZATION ASSAYS

Cytotoxic activity of the toxins and neutralization capacity of the various antibodies were determined by measuring incorporation of $^3$H-leucine into protein in HeLa cells (Keusch et al., 1988, supra). HeLa 229 cell monolayers (ATCC, Rockville, Md.) were grown at 37° C. in McCoy's 5a (modified) medium containing 10% fetal calf serum in 96 well tissue culture plates. Cells were incubated for 3 hr at 37° C. with ST or SLT-II. Some groups were preincubated with polyclonal rabbit antibody or mouse ascites fluid containing mAb to ST (1:60) for 1 hr at room temperature. Following incubation, the wells were washed with leucine-free medium and incubated for a further 30 minutes at 37° C. with $^3$H-leucine (1 μCi/well). The cells were then washed, and 110 μl 0.2M KOH was added to each well for 10 minutes. 100 μl from each well was then added to 1 ml 10% iced trichloroacetic acid and left on ice for 10 minutes before being passed through glass fiber filters (Whatman, Maidstone, England) under suction. The radioactivity retained on the filters was determined after the addition of 4 ml of scintillation fluid (Monofluor, National Diagnostics, Manville, N.J.). $^3$H-leucine incorporation was expressed as a percent of incorporation in the control wells in which the cells had not been exposed to toxin.

ST binding to HeLa cells was determined by growing HeLa cells overnight in microplates as described above, chilling the plates to 4° C., and replacing the medium with 50 μl of fresh medium containing $^{125}$I-toxin. After 1 hr incubation at 4° C., the plates were washed with PBS, the cells disrupted by the addition of 100 μl 0.1M KOH and the radioactivity determined in a Beckman 5500 gamma spectrophotometer (Beckman Instruments, Fullerton, Calif.). Binding was determined by subtracting radioactivity in blank wells (no cells) from that present in wells containing HeLa cells.

6.1.7. IMMUNOPRECIPITATION

Protein was labeled with $^{125}$I using a modification of the chloramine T procedure (Donohue-Rolfe et al., 1984, supra): 1 mCi of carrier-free Na$^{125}$I was added to 10 μg of ST or P1gp in 150 μl of 0.1M sodium phosphate (pH 7.4). 20 μl of a 2.5 mg/ml solution of chloramine T was added, and after a 20 second incubation at room temperature, 20 μl of a 5 mg/ml solution of sodium metabisulfite was added. Rabbit hemoglobin (50 μg/ml) was included as a carrier protein, and bound and unbound label were separated on a 10 ml Sephadex G-25 column (Pharmacia, Uppsala, Sweden). $^{125}$I-labeled protein was stored in 50% glycerol at −20° C.

The competitive inhibition of $^{125}$I-ST binding to the mAb 4D1 by SLT-II was measured as follows. $^{125}$I-ST (1 ng; ~40,000 cpm in 10 μl PBS) was incubated with either mAb 4D1 (one of the new mAbs described herein) in PBS (1:1000), (final volume 100 μl) or with decreasing amounts of SLT-II in the presence of 4D1 (1:1000) (final volume 100 μl). Following 60 minutes of incubation, 1 μl rabbit anti-mouse IgG (Cooper Biomedical, Malvern, Pa.) was added to each reaction mixture and incubated for a further 60 minutes. Antibody-antibody-toxin complexes were immunoprecipitated by adding 50 μl protein A-positive *Staphylococcus aureus* (IgSorb, Genzyme, Boston, Mass.) to each sample. After 10 min, the samples were centrifuged for 2 min in a microfuge (Fisher, Medford, Me.). The pellet was resuspended in a solution of 50 mM Tris (pH 7.4), 5 mM EDTA; 150 mM NaCl with 0.5% Nonidet P-40 (Sigma Chemical Co., St. Louis, Mo.), washed, centrifuged again, and radioactivity in the pellet was determined using a gamma counter. The negative control for these experiments was ascites fluid containing an IgG1 mAb having an unrelated specificity. Results were expressed as a percent of the counts of samples without SLT-II, after subtraction of the counts of the negative controls.

6.2. RESULTS

6.2.1. P1 GLYCOPROTEIN-SHIGA TOXIN INTERACTIONS

FIG. 1 shows the binding of $^{125}$I ST to HeLa cells in the presence of increasing amounts of P1gp-containing HCF of varying degrees of purity. All three P1gp preparations competitively inhibited toxin binding. The most purified P1gp preparation used was approximately 100-fold more effective on a weight basis than the crude cyst material. Not only was binding of toxin affected by P1gp, but in addition, preincubation of ST with crude HCF inhibited cytotoxicity in a concentration-dependent fashion (FIG. 2).

6.2.2. P1 GLYCOPROTEIN AFFINITY PURIFICATION OF SHIGA TOXIN

Figures 3A, 3B:
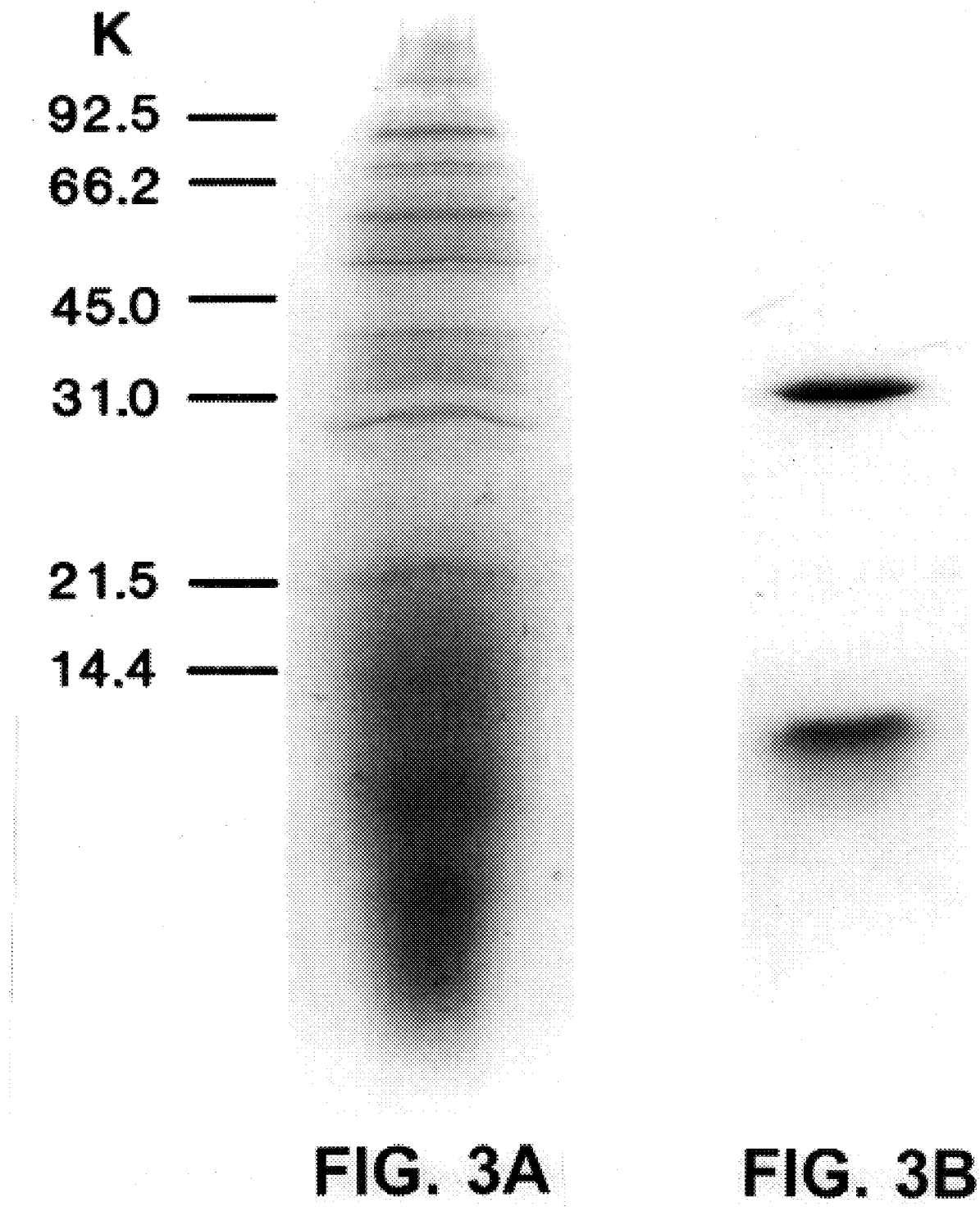

ST was quantitatively adsorbed to a P1gp column and could be eluted with 4.5M MgCl$_2$. Other methods of elution were tried and found unsuccessful, including increasing the pH from 2.5 to 11, or use of 6M urea, 6M guanidine HCl, 50% ethylene glycol, or up to 2M NaCl. The MgCl$_2$ eluate appeared to contain pure ST, and contained only two bands corresponding to the toxin A and B subunits by SDS-PAGE (FIG. 3).

Cytotoxicity of the lysate and eluate was determined by the $^3$H-leucine incorporation assay in HeLa cells. The lysate contained 5.0×10$^5$ ID$_{50}$/mg protein (the amount of toxin inhibiting leucine incorporation by 50%). Following dialysis and lyophilization, the reconstituted eluate contained 3.5× 10$^7$ ID$_{50}$/mg protein, a 700-fold increase in specific activity. Toxin yields were consistently greater than 80% of starting toxin bioactivity.

Receptor analogue affinity chromatography (RAAC) purification of ST was next attempted on fermenter cultures of *S. dysenteriae* type 1, strain 60R. Direct application of large volumes of cell lysate blocked the P1gp column. This was avoided by partial purification of crude ST by ammonium sulfate precipitation and Blue Sepharose chromatography before applying to the P1gp column (Keusch et al., 1988, supra). The MgCl$_2$ eluate again contained only A and B subunits of ST by SDS-PAGE. The yield of ST from three separate 20 l batches of strain 60R is shown in Table I.

TABLE I

YIELD OF SHIGA TOXIN FROM LARGE SCALE
P1 GLYCOPROTEIN AFFINITY-CHROMATOGRAPHY

| | Amount of Toxin (mg) | | |
|---|---|---|---|
| Toxin Preparation | Batch 1 | Batch 2 | Batch 3 |
| Post Ammonium Sulfate | 13.0 | 7.58 | 7.40 |
| Post Blue Sepharose | 10.2 | 6.23 | 6.60 |
| Post P1 Eluate | 9.98 | 5.64 | 6.51 |
| | (77%)[a] | (78%) | (88%) |

[a]Percentage yield of starting toxin was antigen determined by ELISA using a mAb specific for the B subunit (Donohue-Rolfe et al., 1986, supra).

The mean (±1 SD) yield of toxin antigen (by ELISA) was 7.4±2.3 mg per batch, and the mean recovery was 81±6.1%. Purified toxin was also biologically active in the leucine incorporation assay, increasing from an ID$_{50}$ of 1×10$^7$ per mg protein in the ammonium sulfate precipitate to 5.9×10$^{10}$ per mg protein in the MgCl$_2$ eluate from the P1gp column. When loaded to its capacity, as determined by a rising A$^{280}$ in the flow-through, the P1gp column was able to retain 4.5 mg ST/ml gel. The affinity column was reused multiple times (10–20) with no apparent loss of function. However, the column required washing with at least 20 column volumes of 4.5M MgCl$_2$ between runs, to remove trace amounts of toxin.

6.2.3. RECEPTOR ANALOGUE AFFINITY CHROMATOGRAPHY OF SHIGA-LIKE TOXINS

Figures 4A, 4B:
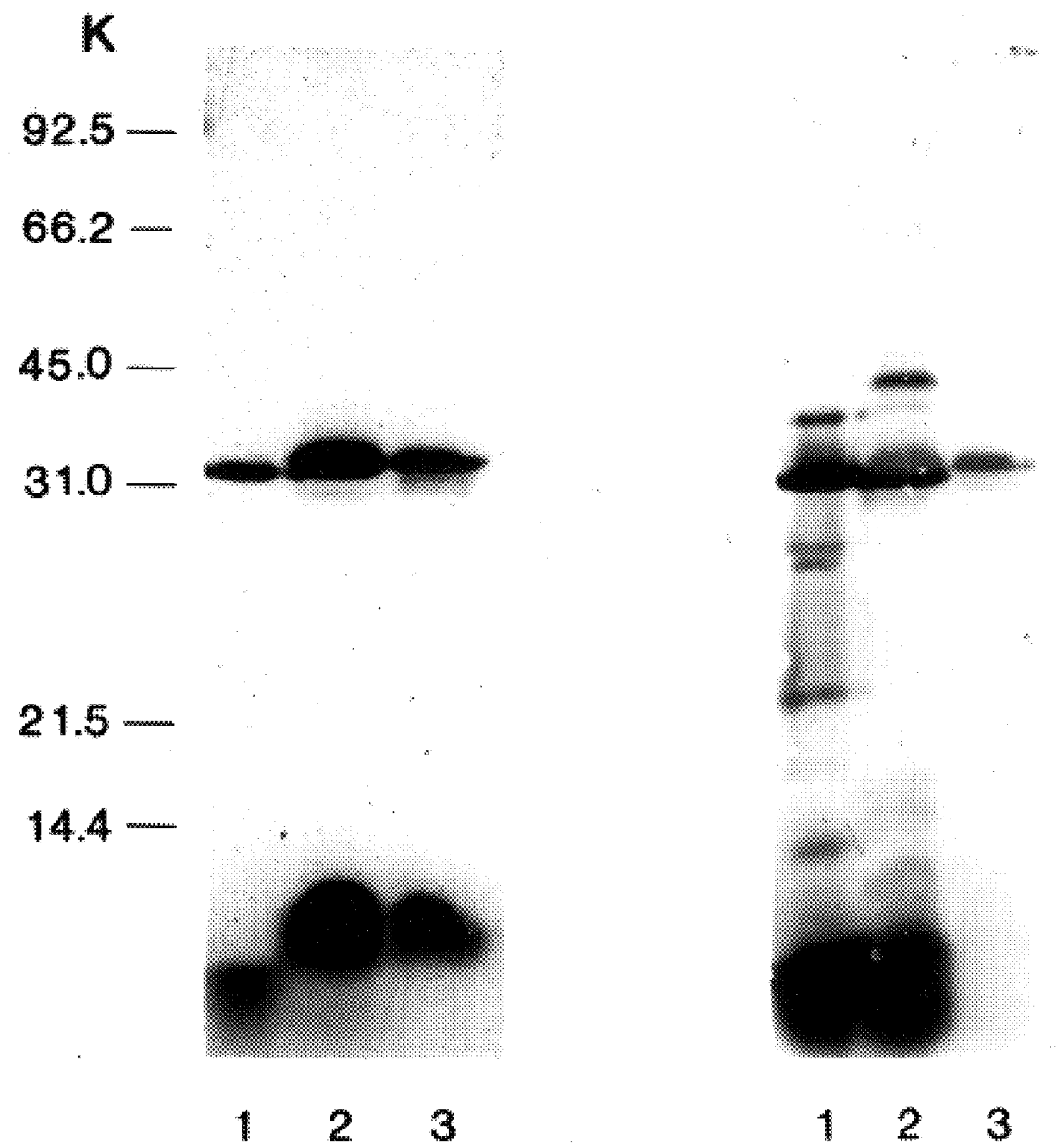

Twenty liters of culture supernatant from an overnight culture of *E. coli* 0157:H7 was processed as described in Section 6.1.3., supra, and passed over a P1gp column. Again, two main bands were detected in the MgCl$_2$ eluate with a molecular weight slightly larger than ST, and corresponding to the reported molecular weights of the A and B subunits of SLT-II (FIG. 4A). Western blot analysis of the same preparation using polyclonal rabbit antibody raised against ST revealed two additional peptide bands corresponding to the A and B subunits of SLT-I (FIG. 4B). The P1gp-purified *E. coli* 0157:H7 supernatant was cytotoxic to HeLa cells. The cytotoxic activity was partially neutralized by the rabbit polyclonal anti-ST antiserum, probably resulting from neutralization of the small amount of cross-reactive SLT-I present in this supernatant.

Purification of toxin from *E. coli* strain C600, containing phage 933W, an organism believed to produce only SLT-II, was performed by the RAAC method exactly as described above. The purified SLT-II contained only the A and B subunits of this toxin, with no contaminating SLT-I observed by SDS-PAGE (FIG. 4A) or in Western blots using the rabbit polyclonal anti-ST antibody (FIG. 4B). The P1gp-purified SLT-II was cytotoxic to HeLa cells, but was not neutralized by the polyclonal rabbit anti-ST.

6.2.4. PREPARATION OF SPECIFIC AND CROSSREACTIVE MONOCLONAL ANTIBODIES

Four mAbs were obtained after immunization of mice with affinity-purified bacterial culture supernatant. Ascites fluid samples from the four hybridomas were screened by a sandwich ELISA method which measured binding to P1gp-purified SLT-II or ST. Three of the four Mabs detected by binding to SLT-II also bound to ST in ELISA. In contrast, mAb 4D3, a previously described B-subunit mAb specific for ST (Donohue-Rolfe et al., 1984, supra) bound to ST but failed to bind to SLT-II in ELISA.

Subunit specificity of these mAbs was tested by Western blot. Two mAbs (3D1 and 4D5) bound to the A subunit of SLT-II and ST. One mAb, 2B1, bound to the B subunit of SLT-II only, and one, 4D1, bound to the B subunit of both SLT-II and ST. The previously described mAb, 4D3, bound to the B subunit of ST but not SLT-II. These ELISA and Wester blot results are summarized in Table II.

TABLE II

PROPERTIES OF MONOCLONAL ANTIBODIES RAISED AGAINST ST AND SLT-II

| mAb | Isotype | ELISA ST | ELISA SLTII | Neutralization ST | Neutralization SLTII | Subunit Specificity ST | Subunit Specificity SLTII |
|---|---|---|---|---|---|---|---|
| 4D1 | IgG1 | + | + | + | + | B | B |
| 2B1 | IgG2b | − | + | − | + | − | B |
| 3D1 | IgM | + | + | − | − | A | A |
| 4D5 | IgM | + | + | − | − | A | A |
| 4D3 | IgG1 | + | − | + | − | B | − |

Figure 5:
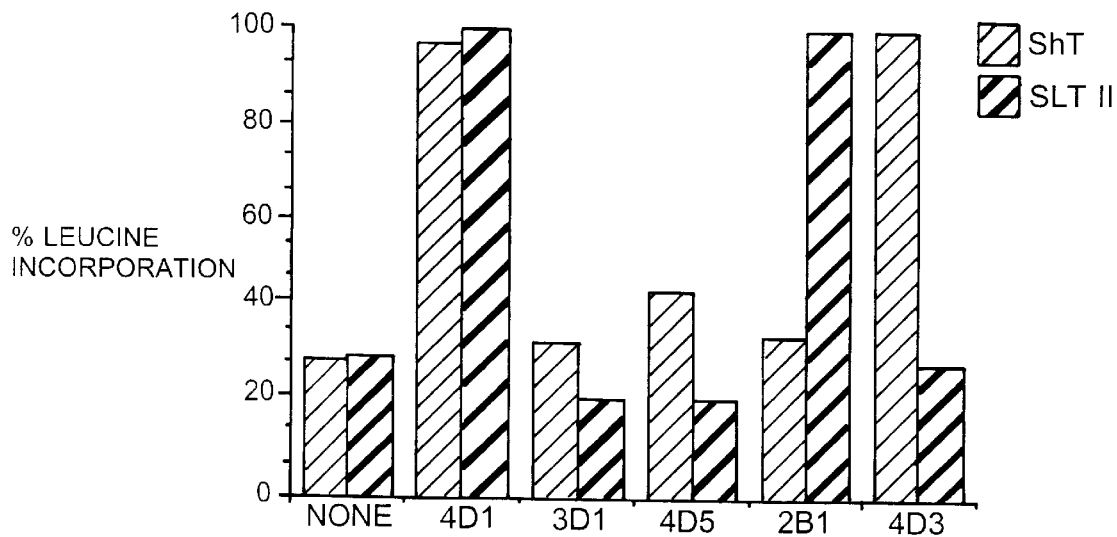
FIG. 5 shows inhibition of incorporation of $^3$H—leucine into HeLa cells in the presence of either ST or SLT-II (expressed as percent of control in the absence of toxin). Toxins were also preincubated with a 1:60 dilution of the mAb-containing ascites fluid and the effect on leucine incorporation was determined in the same manner.

Only 2 of 4 new mAbs, 4D1 and 2B1, neutralized SLT-II in the leucine incorporation assay (FIG. 5). As before, 4D3 strongly neutralized ST, but did not affect SLT-II. Of greatest interest was mAb 4D1, which virtually completely neutralized both SLT-II and ST at a dilution of 1:60. Identical results were obtained with both hybridoma culture supernatants and ascites fluid.

In addition to subcloning twice, mAb 4D1 was subjected to HPLC analysis. Only a single homogeneous peak was observed, consistent with the presence of only one mAb.

Figure 6:
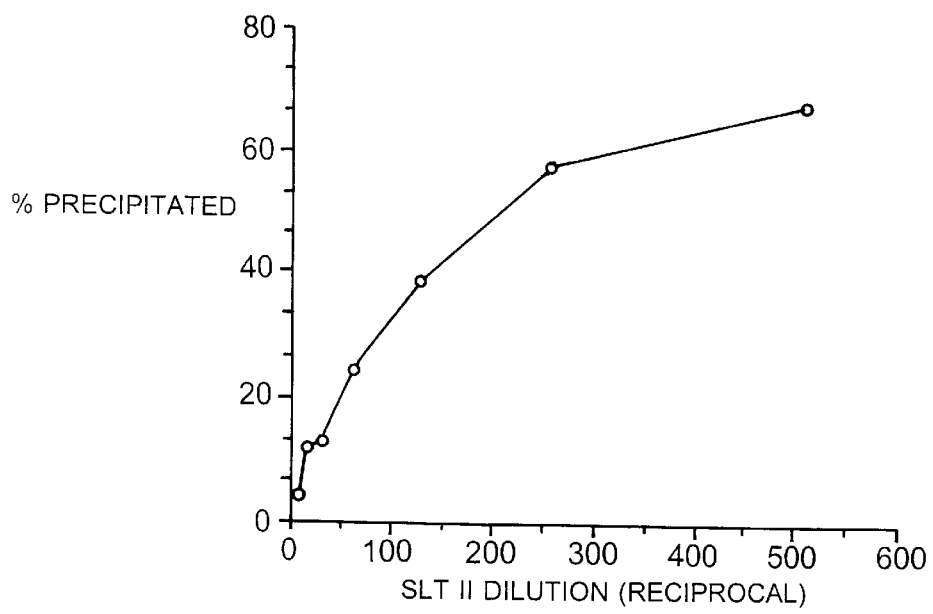
FIG. 6 shows immunoprecipitation of $^{125}$-ST by mAb 4D1 following preincubation with decreasing concentrations of SLT-II. Results are expressed as a percent of the control in the absence of SLT-II.

To further confirm that 4D1 cross-neutralized both SLT-II and ST, competitive inhibition of the immunoprecipitation of $^{125}$I-labelled ST by 4D1 was tested by adding increasing amounts of purified SLT-II. FIG. 6 shows that SLT-II inhibited this immunoprecipitation in a dose related fashion, consistent with competition of the two toxins for binding to the same monoclonal antibody.

7. EXAMPLE 2

Enzyme-Linked Immunosorbent Assay for Shiga Toxin and Shiga-Like Toxin II Using P1 Glycoprotein from Hydatid Cysts Studies described below showed that HCF contained soluble material (termed hydatid cyst material or "HCM") that interacted directly with both ST and SLT-II and potently inhibited ST binding to HeLa cells. In addition, it was found that partially purified P1gp or crude HCM containing P1gp can be used in a solid phase ELISA format (coated to wells of microtiter ELISA plates) to serve as capture ligands for both ST and SLT-II for quantitative assay. This assay is specific for Shiga family toxins, is sensitive in the subnanogram level, and is a simple quantitative new alternative to a tissue culture assay.

7.1. MATERIALS AND METHODS
7.1.1. P1 GLYCOPROTEIN

P1 glycoprotein was purified using the techniques described in Section 6.1.1., above.

7.1.2. BACTERIAL TOXINS

*E. coli* heat-stable ("ST") and heat-labile ("LT") enterotoxins were obtained from Cambridge Research Laboratories (Cambridge, Mass.). Cholera toxin was purchased from List Biological Laboratories (Campbell, Calif.). Diphtheria toxin and tetanus toxin were a gift from Dr. Michael Gill, Tufts University School of Medicine (Boston, Mass.). ST was purified from S. dysenteriae type I strain 60R as described above. SLT-II was purified from an *E. coli* C600 containing the 933W phage (provided by Dr. H. Williams-Smith, Houghton Poultry Research Station, Huntingdon, UK) by affinity chromatography using P1gp coupled to Sepharose 4B as described above in Section 6.1.2. Purified ST and Shiga-like toxin II were quantitated by measuring $A_{280}$ using an absorbance of 1.0 (with a 1 cm light path) equal to 1 mg/ml.

7.1.3. PREPARATION OF POLYCLONAL AND MONOCLONAL ANTIBODIES

Rabbit Antisera to ST and SLT-II were prepared by immunizing rabbits with formalin-treated purified toxin as previously reported (Donohue-Rolfe et al., 1984, supra).

To obtain polyclonal anti-SLT-II sera, mice were injected intraperitoneally (i.p.) with 50 pg of toxoid in Freund's complete adjuvant and then boosted 4 weeks later with 50 pg of the toxoid in incomplete Freund's adjuvant. Three weeks later, mice were sacrificed and immediately bled by cardiac puncture. The toxoid was prepared by formalin inactivation as described by Donohue-Rolfe et al. (1984, supra).

A mAb was obtained by immunizing BALB/C mice with Shiga-toxoid as previously described (Donohue-Rolfe et al., 1984, supra). A hybridoma designated 4D3 produced an IgG1 antibody specific for the B subunit of ST.

7.1.4. ELISA FOR SHIGA TOXIN AND SHIGA-LIKE TOXIN II

Crude sheep HCM was diluted to a protein concentration of 1–10 pg/ml in 50 mM carbonate buffer ($Na_2CO_3$/$NaHCO_3$, pH 9.6). Microplate wells were each inoculated with 200 μl and were incubated overnight at 4° C. Wells were then emptied and each well received 200 μl 1% BSA in carbonate buffer for 1 hour at room temperature, followed by 5 washes with phosphate buffered saline containing 0.05% Tween-20 (pH 7.4) (PBS-T). Test samples of different concentrations of ST or SLT-II in PBS-T (100 μl/well) were added, the plates were incubated for 2 hours at room temperature and then washed in PBS-T at least 5 times. Polyclonal rabbit anti-ST antibody (1:5000) or polyclonal mouse anti-SLT-II antibody (1:1000) was then added, and the plates were incubated for 1 hour at room temperature followed by 5 washes with PBS-T. Finally, antibody binding to the plates was detected by adding enzyme-linked second antibodies. For detection of rabbit anti-ST antibody, 200 μl/well of goat anti-rabbit IgG-alkaline phosphatase conjugate (Sigma Chemical Co., St. Louis, Mo.) (1:1000 in PBS-T) was used. For detection of mouse anti-SLT-II, 100 μl/well of goat anti-mouse Ig-alkaline phosphatase conjugate (Sigma Chemical Co.) (1:350 in PBS-T) was used. After a 1 hour incubation, plates were washed with PBS-T and the alkaline phosphatase substrate, p-nitrophenylphosphate (1 mg/ml solution, 200 μl/well) (Sigma Chemical Co.) in diethanolamine buffer (pH 9.8) was added. The color reaction was assessed as $A_{405}$ using with a microplate colorimeter (BioTek, Burlington, Vt.). Net absorbance was determined by subtracting the $A_{405}$ values in wells treated with PBS-T in place of toxin from the $A_{405}$ values in toxin-containing wells.

7.1.5. GROWTH OF HELA CELLS AND ASSAY FOR TOXIN BINDING

HeLa cells (CCL-2, ATCC, Rockville, Md.) were grown at 37° C. in McCoy's 5a (modified) medium containing 10% fetal calf serum. To measure toxin binding 100 µl of a HeLa cell suspension containing $2\times10^4$ cells were added to each well of a 96 well tissue culture plate (Costar, Cambridge, Mass.). Cells were grown to confluence overnight at 37° C., then chilled to 4° C., followed by removal of the medium by aspiration and replacement with 50 µl of medium containing $^{125}$I-labeled ST (100,000 cpm; 30,000 cpm/ng protein). After a 1 hour incubation at 4° C., wells were washed 5 times with PBS, the cells disrupted by adding 100 µl of 0.1M KOH, and the radioactivity measured in a gamma spectrometer (Beckman Instruments, Fullerton, Calif.). Total binding was determined by subtracting the cpm in blank wells from wells with HeLa cell monolayers.

7.1.6. IMMUNOPRECIPITATION OF TOXIN-P1 GLYCOPROTEIN COMPLEXES

HCF protein was labeled with $^{125}$I using a modification of the chloramine T procedure (Donohue-Rolfe et al., supra): one mCi of carrier-free Na$^{125}$I was added to 10 pg of ST or P1gp in 150 µl of 0.1M sodium phosphate (pH 7.4). Twenty µl of a 2.5 mg/ml solution of chloramine T was added, and after a 20 second incubation at room temperature, 20 µl of a 5 mg/ml solution of sodium metabisulfite was added. Rabbit hemoglobin (50 µg/ml) was included as a carrier protein. Bound and unbound label were separated on a 10 ml Sephadex G-25 column (Pharmacia, Uppsala, Sweden). $^{125}$I-labeled protein was stored in 50% glycerol at -20° C.

7.2. RESULTS

7.2.1. INTERACTION OF SHIGA TOXIN WITH HYDATID CYST MATERIAL

The ability of sheep HCF to inhibit toxin binding to HeLa cells was evidence for the presence of ST binding material which is considered to be a ST receptor analogue. Three ng of crude HCM was sufficient to inhibit ST binding by greater than 90%. The glycoprotein fraction purified from crude HCF on the basis of P1 blood group activity was 100-fold more potent an inhibitor of toxin binding than was the crude material (25 pg inhibited ST binding by over 90%), and there was a concomitant diminution in cytotoxicity.

Pretreatment of HeLa cells with HCM (30 min at 4+ C.) had no effect on radiolabeled toxin binding.

When $^{125}$I-labeled purified P1gp ($1.5\times10^6$ cpm) was incubated with unlabeled ST, followed by addition of polyclonal rabbit anti-ST serum and protein A$^+$ S. aureus to precipitate the toxin, 327,000 cpm were detected in the immunoprecipitate. In contrast when toxin was incubated with normal rabbit serum 24,000 cpm were present in the precipitate. Similarly, when rabbit antiserum or normal serum was incubated with $^{125}$I-labeled P1gp in the absence of toxin, 16,000 cpm and 19,000 cpm were present in the precipitates, respectively. These results demonstrate that a component of the HCF was binding to the toxin.

7.2.2. ELISA FOR SHIGA TOXIN

Since HCM could interacted directly with the toxin, the present inventors exploited this binding to develop an ELISA. To capture the toxin molecule, microplates were coated with crude HCF; polyclonal rabbit anti-ST serum was used as the detection antibody to detect the presence of the toxin. This HCM-based ELISA was compared with an assay in which a mAb specific for the toxin B chain was the capture reagent (FIG. 7). The titers measured in the mAb—capture ELISA correlate well with cytotoxin titers (Donohue-Rolfe et al., 1986, supra), and the mAb capture ELISA detects as little as 38 pg/well of toxin. The HCM capture ELISA detected as little as 80 pg/well ST, with a linear calibration curve between 0.8 and 12 ng toxin/ml. The mAb capture ELISA was consistently more sensitive, but only by a factor of 2. Varying the cyst fluid protein concentration used for the coating between 1 and 100 pg/ml, or using more purified cyst fluid preparations, did not alter assay sensitivity. Decreasing the cyst protein concentration below 1 pg/ml did however markedly reduce sensitivity. Specificity of the assay was determined using other bacterial toxins. No significant absorbance readings were obtained with 1 µg/ml of E. coli LT, E. coli ST, cholera, diphtheria, or tetanus toxins.

7.2.3. ELISA FOR SHIGA-LIKE TOXIN II

To determine if HCM could also be used to capture SLT-II by this ELISA method, microplates were coated with crude HCM as above. Bound SLT-II was detected in a double sandwich format using polyclonal mouse anti-SLT-II serum. The SLT-II ELISA was able to detect as little as 132 pg/well and the calibration curve was linear between 1.32 ng/ml and 21 ng/ml (FIG. 8).

7.3. DISCUSSION

The report by Cameron and Stavely (Cameron et al., supra) that cyst fluid extracted from sheep infected with the cestode Echinococcus granulosus had potent P1 blood group activity, which was later shown to be due to a glycoprotein bearing the terminal trisaccharide determinant of the P1 glycolipid blood group antigen, led to extensive immunochemical study of P blood group antigens. Various methods have been used for the isolation of glycoprotein with P blood group activity. However, to date the protein and carbohydrate components of this apparently heterogeneous group of molecules has yet to be fully characterized. ST was known to bind to two antigens of the P blood group system (Jacewicz et al., supra), the glycosphingolipid pK and P1 antigens, whose structures contain the identical terminal Galα1→4Gal disaccharide as follows:

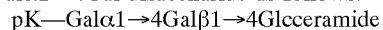
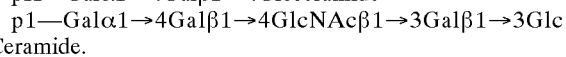

Ceramide.

As described herein, HCF contained a potent competitive inhibitor of ST binding to HeLa cells. The finding that toxin binding inhibitory activity was greatly enriched in a fraction isolated from crude cyst fluid on the basis of its P1 activity indicated that the inhibitor is the P1gp itself. Radiolabeled glycoprotein material from cyst fluid was shown to interact directly with ST. Following this interaction P1gp can be immunoprecipitated by polyclonal rabbit anti-ST antibody. Thus, the mechanism of the inhibition of toxin binding is the direct competition for receptor binding between Galα1→4Gal—containing HeLa cell-surface glycolipids and the Galα1→4Gal—containing soluble material from the HCF.

Microplates coated with crude HCM were able to capture both ST and SLT-II in an ELISA assay. For ST detection, the ELISA was sensitive to as little as 80 pg of toxin protein. The same ELISA was less sensitive for SLT-II, detecting a minimum of 132 pg toxin. The difference in toxin sensitivity between the ST and SLT-II ELISA may be due to the differences in the polyclonal antibodies directed against the two toxins, the polyclonal rabbit anti-ST being a very high titer antibody.

As noted, a common feature of ST, SLT-I and SLT-II is the ability to bind to Galα1→4Gal—containing glycolipid cell-surface receptors present in tissue culture cells and rabbit intestinal microvillus membranes. Polyclonal antibodies directed against ST or SLT-II are reported to be ineffective in cross-neutralizing each other and certain other SLT'S. In contrast, soluble Pi glycoprotein in HCF appear to provide an effective agent for inhibiting the cytotoxic activity of ST, SLT-I, SLT-II, SLT-II variants (described in more detail below), and possibly other as yet undiscovered members of the Shiga family of toxins. The neutralizing ability of P1gp could even be used as a functional basis for defining members of this group of toxins. Furthermore, the binding ability of P1gp forms the basis for a simple antigen-capture ELISA using the crude clarified and dialyzed fluid contents of hydatid cysts.

8. EXAMPLE 3

PURIFICATION AND QUANTITATION OF VARIANTS OF SHIGA-LIKE TOXIN II

In this study, the present inventors examined the binding of two Shiga-like toxin II variants, termed SLT-IIvp and SLT-IIvh, to polystyrene ELISA plates coated with HCM. Having determined that the SLT-II variants were detectable by ELISA using a polyclonal antibody to SLT-II, the present inventors then used P1 affinity chromatography (Donohue-Rolfe, A. et al., *Infect. Immun.* 57:3888–3893 (1989)) to purify SLT-IIvp and SLT-IIvh.

Following purification of the toxins, various ELISA capture systems were compared, including purified glycolipids Gb3 and Gb4, crude HCM and a mAb, 4D1, previously raised to SLT-II (Donohue-Rolfe et al., 1989, supra).

8.1. MATERIALS and METHODS

8.1.1. BACTERIAL STRAINS

Two strains, *E. coli* HB101(pDLW5) which expresses SLT-IIvp (Weinstein, D. L. et al., *J. Bacteriol* 170:4223–4230 (1988)), and *E. coli* DH5α(B2F1) which expresses SLT-IIvh (Samuel, J. E. et al., *Infect. Immun.* 58:61–-618 (1990)), were provided by Dr. Alison O'Brien, Department of Microbiology, Uniformed Services University of the Health Sciences, Bethesda, Md.

8.1.2. SMALL SCALE CULTURES

Initially both bacterial strains were grown in small volumes (<30 ml), in either modified syncase medium (Keusch, G. T. et al., 1988, supra) or Luria Bertani medium, by making an inoculum from a stationary phase culture. Cultures were then grown overnight at 37° C. with shaking (200 rpm). Following overnight culture, the supernatant was removed by centrifugation in a microfuge, and the pellet was resuspended in PBS and disrupted by sonication. The culture supernatants and cell lysates were then assessed for the presence of the toxin by ELISA and cytotoxicity.

8.1.3. QUANTITATION OF SLT-IIvp AND SLT-IIvh BY ELISA USING VARIOUS CAPTURE SYSTEMS

Four different toxin capture systems were examined:
(1) hydatid cyst material (HCM), 10 μg/ml, dissolved in PBS and coated overnight at 4° C. (Acheson, D. W. K. et al., *J. Infect. Dis.* 161:134–137 (1990));
(2) ascites fluid containing mAb 4D1 diluted in PBS (1:2000) and coated overnight at 4° C.;
(3) Gb3 (Marreya; Pleasant Gap, Pa.) at 10 μg/ml methanol, allowed to evaporate at 37° C.;
(4) Gb4 (Marreya) at 10 μg/ml methanol, allowed to evaporate at 37° C.

NUNC Maxisorp Immunoplates (NUNC, Denmark) were used for the HCM and 4D1 capture assays. Immulon 3 plates (Dynatech, Chantilly, Va.) were used for the Gb3 and Gb4 capture assays. All capture reagents were added at 100 μl/well. Once plates were coated, the assays were carried out identically except for temperature. Gb3 and Gb4 assays were done at 37° C. whereas the HCM and 4D2 assays were at room temperature. Plates were blocked with 1% BSA in PBS, and following washes with PBS-0.5% Tween-20, the toxin-containing solutions were added at 100 μl/well. Toxin bound to the wells was detected using a rabbit polyclonal antibody specific for SLT-II (or, a polyclonal anti-ST antibody for ST) followed by a goat anti-rabbit IgG alkaline phosphatase-conjugated second antibody and then substrate (Acheson, D. W. K. et al., supra).

8.1.4. LARGE SCALE CULTURES

Following the small scale cultures HB101(pDLW5) and DH5α(B2F1) were grown separately in 9.9 liter fermenter cultures (fermenter model MF128S; New Brunswick Scientific Co., Inc., Edison, N.J.). LB medium was used for HB101(pDLW5) and modified syncase medium was used for DH5α(B2F1). Following overnight growth, the cultures were harvested and bacteria concentrated using Pellicon tangential flow membrane filtration (0.45μ Durapore filter, Millipore Corp., Bedford, Me.). The supernatants harvested from the fermenter cultures were ultraconcentrated by passage over a 10 kDa molecular weight cut-off ultrafiltration membrane in a Pellicon apparatus. The concentrate was washed with 1.51 of 10 mM Tris-HCl, pH 7.5, then treated with ammonium sulfate to 60% saturation. After overnight incubation at 4° C., the precipitate was collected by centrifuging at 13,200 x g for 20 min, resuspended in 10 ml of 10 mM PBS (pH 7.5) and dialyzed with 3 changes of 41 of the same buffer over 24 hours.

8.1.5. LARGE SCALE PURIFICATION

SLT-IIvp and SLT-IIvh were purified from the ammonium sulfate precipitate of the culture supernatant concentrates as described above using a P1gp-Sepharose 4B column (see, also Donohue-Rolfe et al., 1989, supra). Briefly, aliquots of the reconstituted and dialyzed precipitate were applied to a 3 ml P1gp-Sepharose 4B column. Following washes with PBS and 1M NaCl, toxin was eluted using 4.5M $MgCl_2$ and dialyzed against ammonium bicarbonate.

8.1.6. CYTOTOXICITY ASSAYS

Both the crude cell lysates and culture supernatants, as well as the purified toxins, were tested for cytotoxicity to Vero and HeLa 229 cells (ATCC, Rockville, Md.) using the $^3$H-leucine incorporation assay as described above. (See, also, Keusch, et al., 1988, supra.) Following trichloracetic acid precipitation, the cellular proteins were harvested using a Multiscreen filtration system (Millipore Corp., Bedford, Me.).

8.1.7. BIOCHEMICAL ANALYSES

Protein concentrations for the purified toxins were determined using the method of Lowry (Lowry, O. H. et al., *J. Biol. Chem.* 193:265–275 (1951)). Protein concentrations from HeLa and Vero cell extracts were determined using the BioRad (BioRad, Rockville, N.Y.) assay with BSA as a standard.

SDS-PAGE was performed in 8 cm×0.75 cm slab gels using standard techniques and stained with Coomassie brilliant blue stain.

High performance liquid chromatography of HeLa and Vero cell glycolipid extracts was performed as follows. Glycolipids were extracted from scraped pellets of HeLa and Vero cells by chloroform:methanol extraction and purified by phase partitioning, Unisil chromatography (Clarkson Chemical Co., Willamsport, Va.) and hydrolysis of phospholipids as described previously (Jacewicz, M. et al., *J. Infect. Dis.* 159:881–889 (1989)). The samples were quantitated following benzylation using HPLC on a 50 cm Zipax column (Dupont, Wilmington, Del.) fitted to a Beckman HPLC (Beckman Instruments, Fullerton, Calif.) attached to a monitor reading absorption at 229 nm. Elution was achieved using 2 to 46% linear gradient of hexane to 46% dioxane/hexane (Ulman, D. et al., *Methods in Enzymology* 138:117–125 (1987)). The glycolipid content of the samples was analyzed using Beckman system Gold software (Beckman Instruments, Fullerton, Calif.).

8.2. RESULTS

8.2.1. BACTERIAL CULTURES AND TOXIN PURIFICATION

Culture supernatants and cell lysates from small scale cultures of HB101(pDLW5) and DH5α(B2F1) grown in modified syncase medium and Luria Bertani (LB) medium respectively, contained material which could bind to crude HCM, and was detectable using polyclonal antibodies raised to SLT-II.

Toxins were purified from supernatants of 9.9 liter fermenter batches of HB101(pDLW5) and DH5α(B2F1) as described above. Two fermenter batches of each strain were processed and yielded 0.16 mg/l of culture of purified SLT-IIvp from HB101 (pDLW5) supernatant, and 0.12 mg/l of culture of purified SLT-IIvh from the DH5α(B2F1) supernatant. The overall yields from the two cultures, determined by measuring the amount of toxin in the culture supernatant compared with the amount following dialysis of the $MgCl_2$ eluate, was high (70% and 65% for SLT-IIvh and SLT-IIvp, respectively).

Analysis by 15% SDS-PAGE revealed that both proteins were composed of two peptides, corresponding to A and B subunits, as expected (FIG. 9). The larger A subunit of the toxin derived from each strain had an apparent MW of 32 kDa. The smaller B subunit from pDLW5 had an apparent MW very similar to that of ST (7.5 kDa). In contrast, the B subunit from B2F1 which was larger, and its migration in SDS-PAGE more closely resembled the SLT-II B subunit (10 kDa) (FIG. 9).

8.2.2. CYTOTOXIC ACTIVITY OF SLT-II VARIANTS

Crude cell lysates and the purified proteins were tested for cytotoxicity on HeLa and Vero cells, and compared with ST purified by P1gp affinity chromatography. HeLa 229 cells were sensitive to all the toxins, showing a characteristic log-linear dose response over a wide range of toxin concentrations (FIG. 10A). The dose-response curves were parallel for all toxins studied, with ST being the most active (Table III, below). The cytotoxicity curves for Vero cells had a different shape from those of the HeLa 229 cells, with a steep rise in sensitivity of the cells over a narrow range of toxin concentrations (FIG. 10B). Vero cells were about 5-fold more sensitive than HeLa 229 cells to the effects of the SLT-II variant toxins, but were less sensitive to ST (Table III).

TABLE III $ID_{50}$s of purified toxins on HeLa and Vero cells (ng/ml) as determined by inhibition of $^3$H-leucine incorporation.

| Toxin | Target Cells | | Fold Increase in Vero Sensitivity |
|---|---|---|---|
| | HeLa | Vero | |
| Shiga toxin | 0.05 | 0.03 | 1.6 |
| SLT-IIvp | 0.2 | 0.03 | 6.6 |
| SLT-IIvh | 0.3 | 0.07 | 4.3 |

8.2.3. GLYCOLIPID CONTENT OF HeLa AND VERO CELLS

Gb3 and Gb4 were found in both HeLa 229 and Vero cells (FIG. 11A and 11B). Gb3 content was similar (1300 pmoles Gb3/mg protein in HeLa vs. 1456 pmoles Gb3/mg protein in Vero). In contrast, HeLa 229 cells contained approximately half as much Gb4 as did Vero cells (536 vs. 1191 pmoles/mg protein).

8.2.4. MEASUREMENT OF TOXINS IN AN ELISA CAPTURE FORMAT

The 4 solid phase ELISA capture systems, utilizing HCM, mAb 4D1, Gb3 and Gb4, were compared for their ability to capture ST, SLT-II, and the two SLT-II variants purified above.

HCM bound all four toxins to a similar degree (FIG. 12A), and could detect toxin concentrations as low as 0.5 ng/ml.

Figure 12A:
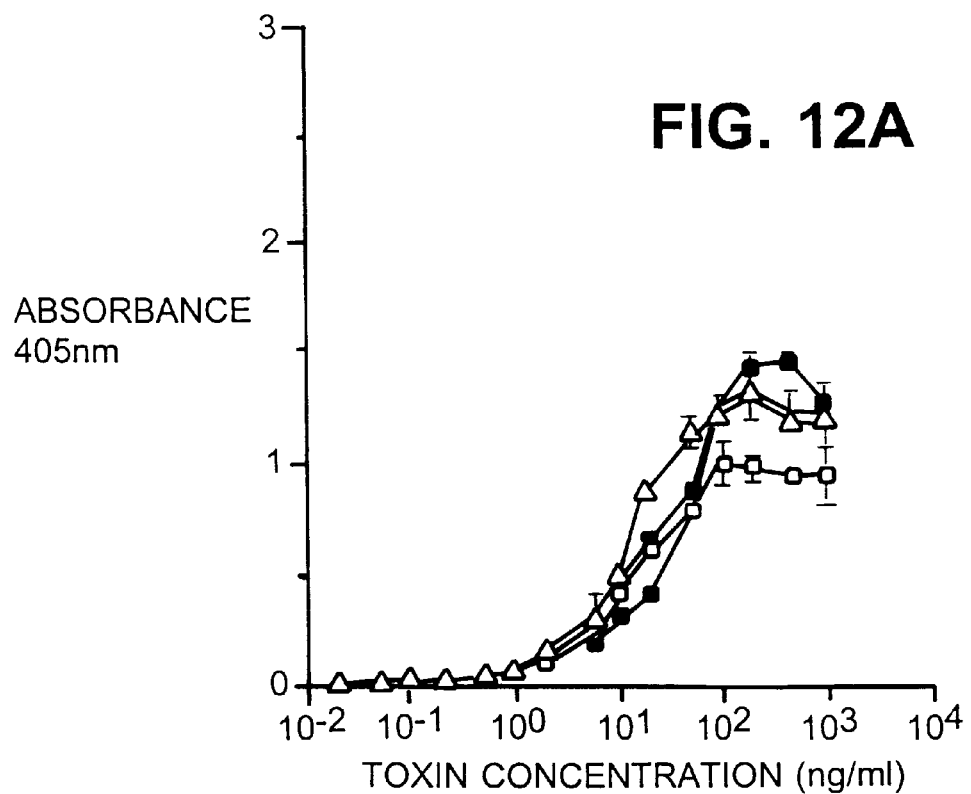
Figure 12B:
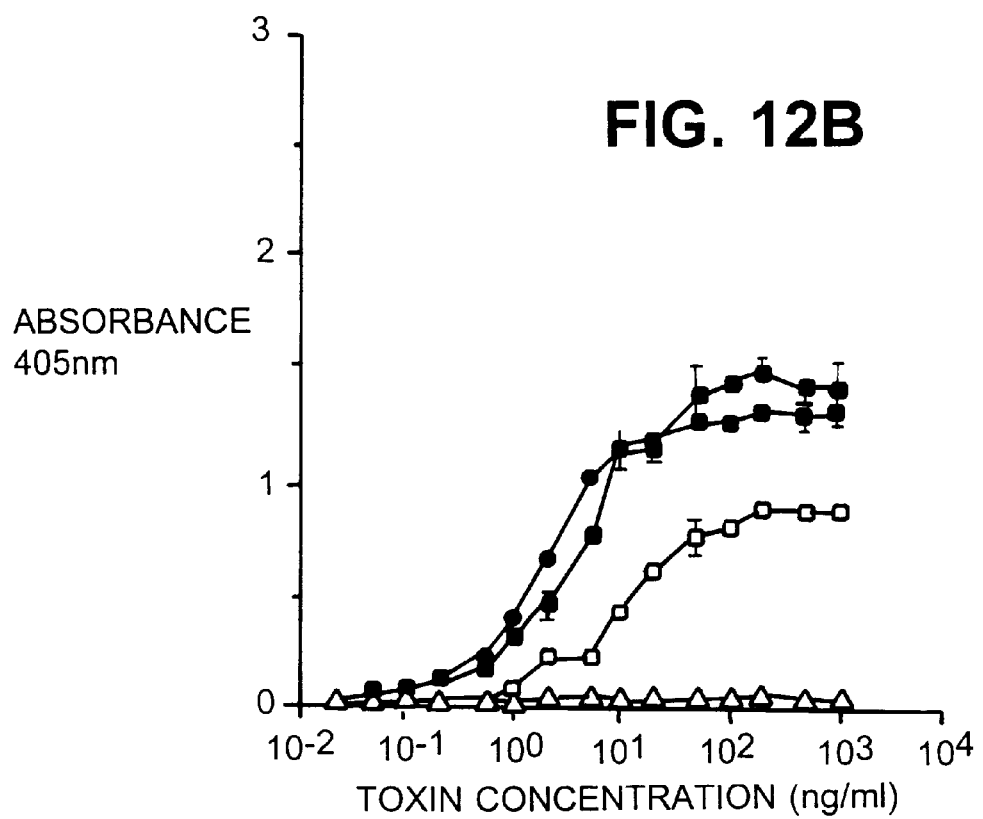

The mAb 4D1 bound both SLT-II and ST, as expected from the results described above (see, also, Donohue-Rolfe et al., 1989, supra). 4D1 could detect as little as 0.5 ng/ml of SLT-IIvh from DH5α(B2F1). However, 4D1 did not bind SLT-IIvp from HB101(pDLW5)(FIG. 12B).

Gb3 detected ST at a sensitivity of <0.02 ng/ml. None of the other toxins were detectable when Gb3 was the capture reagent (FIG. 12C).

In a Gb4 capture ELISA, SLT-IIvp was detectable at 0.1 ng/ml, whereas non of the other toxins could be detected (FIG. 12D).

8.3. DISCUSSION

The present inventors have shown that crude HCM, coupled to Sepharose 4B, can bind both ST and SLT-II, thus enabling a one-step purification procedure. The present inventors also found that both crude SLT-IIvp and SLT-IIvh bound to solid-phase HCM (polystyrene ELISA plates) and were detected using polyclonal antibodies raised against SLT-II.

HCM is a largely uncharacterized mixture of proteins and carbohydrates although it is known to contain P1 blood group reactive glycoproteins (Cameron et al., supra) with the same terminal Galα1→4Gal disaccharide (Watkins et al., supra) as Gb3. In view of the known binding characteristics of SLT-IIvp and SLT-IIvh, both of which are reported to bind to Gb3, the present inventors predicted that these two toxins would bind to the P1gp component of HCM. Based on this prediction, the present inventors successfully purified significant amounts of both SLT-IIvp and SLT-IIvh by affinity chromatography using an HCM affinity matrix.

Toxin proteins eluted from the HCM affinity column were each shown to contain A and B subunits. When examined by SDS-PAGE, the A and B subunits of SLT-IIvh had characteristics very similar to SLT-II (Oku et al., supra).

The SLT-IIvp A subunit ran on SDS-PAGE like the A subunit of SLT-II and SLT-IIvh, whereas the B subunit appeared to be a smaller molecule, more similar in size to the ST B subunit.

Others have shown that, although SLT-IIvp and SLT-IIvh can bind to Gb3, SLT-IIvp bound preferentially to Gb4 (DeGrandis, S. et al., supra) whereas SLT-IIvh bound strongly to Ga2 (Samuel et al., supra) indicating that Gb3 was not the preferred glycolipid. Based on this information, it is not certain whether or not SLT-IIvp and SLT-IIvh bind to Gb3-like molecules in the HCM, or to other digalactosyl glycoproteins in HCM, including Gb4—and Ga2-like glycoproteins. It is also possible that HCM contains a variety of glycoproteins other than those with a terminal Galα1→4Gal disaccharide, or that a combination of these carbohydrate structures presents a more effective binding site than the purified constituents bound to a the polystyrene of an ELISA plate.

Since the toxins had been purified using HCM, HCM-coated plates predictably captured ST, SLT-II, SLT-IIvp and SLT-IIvh, all at concentrations of less than 1 ng/ml.

However, mAb 4D1, directed toward the B subunit of SLT-II and ST, recognized SLT-IIvh, but not SLT-IIvp. This indicates that the B subunits of ST, SLT-II and SLT-IIvh share immunodominant homologies not present in SLT-IIvp.

In contrast, Gb3-coated plates captured only ST, whereas Gb4-coated plates captured only SLT-IIvp. Moreover, the sensitivity of ST detection was approximately 10-fold greater in the present Gb3 capture ELISA than that in assays reported by others (Ashkenazi, S. et al., *J. Clin. Micro.* 27:1145–1150 (1989).

While SLT-II (Waddell et al., supra), SLT-IIvh (Samuel et al., supra), and SLT-IIvp (DeGrandis et al., supra) are all reported to bind to Gb3, the present results suggest that Gb3 is not the ELISA capture system of choice for identification or quantitation of these toxins.

Use of an HCM affinity matrix as described herein enabled the purification of milligram quantities of apparently pure SLT-IIvh and SLT-IIvp from 9.9 liter fermenter cultures. The purified toxins were biologically active cytotoxins which inhibited cellular protein synthesis. The SLT-IIvp and SLT-IIvh purified as described herein were more cytotoxic to Vero cells than to HeLa 229 cells, although the $ID_{50}$ was only about 5-fold greater for the two toxins on this particular HeLa cell line. This difference in toxicity for the two cells lines is markedly less than the 1000-fold difference with SLT-IIvh and 10,000-fold difference with SLT-IIvp that was reported by others (Samuel et al., supra). This discrepancy is thought to result from the fact the HeLa cells used by Samuel et al. (supra) did not express Gb4, while the cells used here expressed both Gb3 and Gb4.

To summarize, the present inventors purified biologically active SLT-IIvp and SLT-IIvh to homogeneity using hydatid cyst material coupled to Sepharose 4B and demonstrated that HCM, the mAb 4D1, and the glycolipids Gb3 and Gb4 can be employed as capture reagents to quantitate SLT-IIvp and SLT-IIvh in an ELISA assay.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for detecting a toxin selected from the group consisting of shiga toxin and shiga-like toxin II in a sample, the method comprising:

a) contacting the sample with a capture reagent bound to a solid phase support under conditions wherein the capture reagent specifically binds the toxin, the capture reagent being selected from the group consisting of: hydatid cyst material, P1 glycoprotein, and globotriosylceramide (Gb3);

b) contacting the solid phase support to which the toxin has bound with a monoclonal antibody which specifically binds both shiga toxin and Shiga-like toxin II;

c) detecting the presence or the absence of the monoclonal antibody bound to the solid phase support, wherein the presence of the monoclonal antibody indicates the presence of the toxin in the sample.

2. The method of claim 1, wherein the capture reagent is Gb3.

3. The method of claim 1, wherein the capture reagent is hydatid cyst material or P1 glycoprotein.

4. A method for detecting a toxin selected from the group consisting of shiga toxin and shiga-like toxin II in a sample, comprising:

a) contacting the sample with a first monoclonal antibody bound to a solid phase support under conditions wherein the toxin specifically binds the first monoclonal antibody;

b) contacting the solid phase support to which the toxin has bound with a second monoclonal antibody which specifically binds both shiga toxin and shiga-like toxin II;

c) detecting the presence or the absence of the second monoclonal antibody bound to the solid phase support, wherein the presence of the second monoclonal antibody indicates the presence of the toxin.

5. The method of claim 4, wherein the second monoclonal antibody binds the B subunit of both shiga toxin and shiga-like toxin II.

6. A kit for detecting a toxin selected from the group consisting of shiga toxin and shiga-like toxin II, the kit being compartmentalized to receive in close confinement therein one or more containers, said kit comprising:

a) a first container means containing a capture reagent which binds to shiga toxin or shiga-like toxin II, the capture reagent being selected from the group consisting of hydatid cyst material, P1 glycoprotein, and globotriosylceramide (Gb3); and b) a second container means containing a monoclonal antibody which specifically binds both shiga toxin and shiga-like toxin II.

7. The kit of claim 6, wherein the capture reagent is Gb3.

8. The kit of claim 6, wherein the capture reagent is hydatid cyst material or P1 glycoprotein.

9. The kit of claim 6, wherein the capture reagent is bound to a solid phase support.

10. The kit of claim 6, further comprising:

c) a third container means containing a detectably labeled antibody which specifically binds the monoclonal antibody.

11. The kit of claim 10, wherein the label is an enzyme.

12. The kit of claim 11, further comprising:

d) a fourth container means containing a substrate for the enzyme.

13. A monoclonal antibody which specifically binds both shiga toxin and shiga-like toxin II.

14. The monoclonal antibody of claim 13, wherein the antibody recognizes the same epitope that is recognized by the antibody secreted by the cells deposited as ATCC Accession No. HB 12452.

15. The monoclonal antibody of claim 14, wherein the monoclonal antibody is secreted by the hybridoma deposited as ATCC Accession No. HB 12452.

16. A hybridoma which secretes the monoclonal antibody of claim 13.

17. A hybridoma which secretes the monoclonal antibody of claim 14.

18. The hybridoma deposited as ATCC Accession No. HB 12452.

19. A method for detecting a toxin selected from the group consisting of shiga toxin and shiga-like toxin II in a sample, the method comprising:
   a) contacting the sample with a capture reagent bound to a solid phase support under conditions wherein the capture reagent specifically binds the toxin;
   b) contacting the solid phase support to which the toxin has bound with a monoclonal antibody which specifically binds both shiga toxin and Shiga-like toxin II;
   c) detecting the presence or the absence of the monoclonal antibody bound to the solid phase support, wherein the presence of the monoclonal antibody indicates the presence of the toxin in the sample.

20. A kit for detecting a toxin selected from the group consisting of shiga toxin and shiga-like toxin II, the kit being compartmentalized to receive in close confinement therein one or more containers, said kit comprising:
   a) a first container means containing a capture reagent which binds to shiga toxin or shiga-like toxin II; and
   b) a second container means containing a second monoclonal antibody which specifically binds both shiga toxin and shiga-like toxin II.

* * * * *